US010646121B2

United States Patent
Narasimhan et al.

(10) Patent No.: US 10,646,121 B2
(45) Date of Patent: May 12, 2020

(54) PRESSURE MEASUREMENT DESIGNS

(71) Applicant: Apple Inc., Cupertino, CA (US)

(72) Inventors: Ravi K. Narasimhan, Sunnyvale, CA (US); Zijing Zeng, San Jose, CA (US); Zhipeng Zhang, Santa Clara, CA (US)

(73) Assignee: Apple Inc., Cupertino, CA (US)

( * ) Notice: Subject to any disclaimer, the term of this patent is extended or adjusted under 35 U.S.C. 154(b) by 614 days.

(21) Appl. No.: 15/274,183

(22) Filed: Sep. 23, 2016

(65) Prior Publication Data

US 2017/0086686 A1 Mar. 30, 2017

Related U.S. Application Data

(60) Provisional application No. 62/234,510, filed on Sep. 29, 2015.

(51) Int. Cl.
*A61B 5/021* (2006.01)
*A61B 5/00* (2006.01)

(52) U.S. Cl.
CPC ........ *A61B 5/02141* (2013.01); *A61B 5/6824* (2013.01); *A61B 5/6831* (2013.01); *A61B 2562/0214* (2013.01); *A61B 2562/0247* (2013.01); *A61B 2562/046* (2013.01)

(58) Field of Classification Search
CPC . A61B 5/02141; A61B 5/6831; A61B 5/6824; A61B 2562/046; A61B 2562/0247; A61B 2562/0214
See application file for complete search history.

(56) References Cited

U.S. PATENT DOCUMENTS

| | | | |
|---|---|---|---|
| 4,896,676 A | 1/1990 | Sasaki et al. | |
| 5,090,246 A * | 2/1992 | Colla | G01L 9/0072 361/283.4 |
| 6,006,386 A | 12/1999 | Mohaupt et al. | |
| 6,435,926 B1 * | 8/2002 | Yeh | A63B 31/11 441/64 |
| 6,491,647 B1 | 12/2002 | Bridger et al. | |
| 7,069,791 B2 | 7/2006 | Hashimoto et al. | |
| 7,306,563 B2 | 12/2007 | Huang et al. | |
| 7,938,025 B2 | 5/2011 | Shimomoto et al. | |

(Continued)

FOREIGN PATENT DOCUMENTS

| | | | |
|---|---|---|---|
| CA | 2665555 A1 * | 11/2010 | G01L 1/146 |
| CN | 101730841 | 6/2010 | |

(Continued)

*Primary Examiner* — Jacqueline Cheng
*Assistant Examiner* — Tho Q Tran
(74) *Attorney, Agent, or Firm* — Kilpatrick Townsend & Stockton LLP

(57) ABSTRACT

The present invention generally relates to the measuring and monitoring of blood pressure. More specifically, embodiments may apply the theory of applanation tonometry for the measurement of blood pressure. Some embodiments provide a method for measuring mean arterial pressure. Some embodiments provide a device that may be worn by a user that may non-invasively measure and monitor blood pressure of a user. In some embodiments, the invention generally relates to sensor arrays for use with a wrist-worn device to measure blood pressure. Embodiments of the sensor array designs described may be configured to improve resolution by decoupling nodes of the sensor array.

39 Claims, 14 Drawing Sheets

(56) References Cited

U.S. PATENT DOCUMENTS

| | | | | |
|---|---|---|---|---|
| 2002/0118027 A1* | 8/2002 | Routkevitch | ........... | A61L 27/06 |
| | | | | 324/694 |
| 2005/0038347 A1 | 2/2005 | Suzuki et al. | | |
| 2007/0257821 A1* | 11/2007 | Son | .......... | G06F 3/016 |
| | | | | 341/22 |
| 2009/0004767 A1 | 1/2009 | Parks et al. | | |
| 2009/0151478 A1* | 6/2009 | Shimomoto | ........... | A61B 5/021 |
| | | | | 73/862.626 |
| 2010/0282000 A1* | 11/2010 | Gorjanc | ................ | G01L 1/146 |
| | | | | 73/862.046 |
| 2011/0096025 A1* | 4/2011 | Slobodin | ................ | G06F 3/044 |
| | | | | 345/174 |
| 2014/0081160 A1 | 3/2014 | Xiang et al. | | |
| 2015/0112606 A1 | 4/2015 | He et al. | | |
| 2015/0164351 A1 | 6/2015 | He et al. | | |
| 2015/0301642 A1* | 10/2015 | Hanauer | ............... | G06F 3/0414 |
| | | | | 345/174 |
| 2017/0356812 A1* | 12/2017 | Madden | ................ | G06F 3/044 |

FOREIGN PATENT DOCUMENTS

| | | |
|---|---|---|
| CN | 102866813 | 1/2013 |
| CN | 103743503 | 4/2014 |
| CN | 104145240 | 11/2014 |
| CN | 204286649 | 4/2015 |
| CN | 104729769 | 6/2015 |
| EP | 2542149 | 4/2014 |

* cited by examiner

PRESSURE MEASUREMENT DESIGNS

CROSS REFERENCE TO RELATED APPLICATION DATA

The present application claims the benefit of U.S. Provisional Appln. No. 62/234,510 filed Sep. 29, 2015; the full disclosure which is incorporated herein by reference in its entirety for all purposes.

BACKGROUND OF THE DISCLOSURE

The present disclosure generally relates to the measuring and monitoring of pressure (e.g., blood pressure or the like). More specifically, embodiments may utilize applanation tonometry for the measurement of blood pressure. Some embodiments provide a method for measuring mean arterial pressure. Optionally, some embodiments provide for a method of measuring and/or monitoring a blood pressure waveform morphology. Some embodiments provide a device that may be worn by a user that may non-invasively measure and monitor blood pressure of a user.

Measuring pressure may be useful in monitoring one or more user parameters. For example, blood pressure measurements may be a helpful user parameter to measure as elevated blood pressure (a.k.a. hypertension) may be an indicator for potential health issues. As a result, blood pressure measurement is a routine test in many medical examinations. Additionally, pressure measurements may also be indicative of a user's heart rate. Further, in some instances, pressure measurements may provide blood pressure waveform morphologies which may be a useful user parameter to monitor.

Embodiments of the present disclosure may provide pressure measurements for monitoring one or more user parameters.

SUMMARY OF THE DISCLOSURE

The present disclosure provides non-invasive devices and methods for determining a blood pressure within a cardiovascular system of a user. In some embodiments, the disclosure generally relates to sensor arrays for use with a wrist-worn device to measure blood pressure. The sensor array may have a plurality of capacitive nodes each formed by an overlapping area of two electrodes. The capacitance at each node may be measured as a representation of the pressure applied at that node. A sensor array may increase the chance of proper placement of at least one pressure sensing node relative to the target artery. Some embodiments reduce the coupling (or cross-talk) between nodes of the sensor array to increase a pressure-sensing resolution of the sensor array. These devices may help reduce issues with signal processing as one or more preferred pressure sensing nodes of the sensor array may be identified and pressure signals received therefrom may require less error correction or processing. Such devices may provide a more convenient and accurate blood pressure monitoring device and may thereby increase the adoption of non-clinical measurements and monitoring of blood pressure by common consumers.

Particular embodiments of the sensor array designs described herein may be configured to improve signal resolution by decoupling nodes of the sensor array. The sensor arrays may be provided on a skin-engaging surface of the wrist-worn device and may be coupled with an actuator for urging the sensor array against the artery of a user (e.g., for an applanation tonometry sweep). The nodes of the array may be sized and sensitive enough to detect a heart-beat pulse and/or a blood pressure of a user (e.g., from the user's radial artery) with minimal adjustment. In some exemplary embodiments, nodes of the array may have a sensing area of approximately 1 mm by 1 mm and the sensor array may define a sensing area of approximately 10 mm×10 mm.

The sensor array may include a first layer of parallel electrodes backed by a backing film, such as a polyimide (e.g. Kapton) film and a second layer of parallel electrodes running transverse or perpendicular to the first layer. The intersections of the rows of parallel electrodes with the columns of parallel electrodes may form each of the nodes the sensor array. Put in another way, the intersections of the rows and columns of electrodes may form the active area of each of the capacitive nodes. These two layers of electrodes may be separated by compressible material such as a dielectric material (e.g., silicone or the like).

In some embodiments, the dielectric material may form separate pillars that are located in the active area of each node (i.e., at the intersections of the first layer of electrodes and the second layer of electrodes). Pillars of dielectric may be provided at these intersections to support the top electrode strips relative to the bottom electrode strips. The dielectric pillar may reduce cross-talk (also referred to as coupling) between the adjacent nodes so that discrete pressures applied at one node are not detected (or minimally detected) at adjacent nodes. This increase in resolution/granularity for pressure signals from the array may be advantageous for identifying one or more nodes of the sensor array best positioned out of the array of nodes relative to the radial artery for measuring a user's pulse and/or blood pressure during applanation tonometry. This may be determined, for example, by identifying one or more nodes measuring the greatest pressure change due to the pulse of the user when the sensor array is applied generally to a target artery region. After identifying the one or more nodes best suited for measuring a patient's pulse, more accurate blood pressure measurements may be performed using the signals from the identified nodes.

In additional embodiments, strips of dielectric may run in the gaps between the column and/or row electrodes. In this dielectric strip configuration, an air gap may be disposed in the intersection between the two plates of the capacitive nodes allowing the nodes to be more sensitive to displacements due to outside forces. The electrode backing material (e.g., Kapton film or the like) may be a relatively stiff material and may introduce some cross-talk between adjacent nodes. For example, deformation of the backing material at one point may be detected at adjacent areas. Accordingly, in some embodiments, slits in the backing material may be provided (e.g., via laser cutting or the like) to reduce this coupling introduced by the backing film. The backing film may be cut to include primary slits in the film between the parallel strips of electrodes so as to provide decoupling between the strips of electrodes. Additionally lateral slits from the primary slits may be provided to increase decoupling along the electrode strips. In some embodiments, the lateral slits may be staggered and may extend in a direction transverse to the primary slits (e.g., perpendicular or non-perpendicular to the primary slits). In some embodiments, the wrist-worn device may align the primary slits along the length of the user's arm such that the distal/top electrode strips are generally parallel to the target artery of the user or aligned with the length of the user's arm (or within 85% of an axis of the blood flow or length of the user's arm). The primary slits may be generally transverse or perpendicular to a length of a band of the wrist-worn device or a longitudinal axis of the device (i.e., along the circumference of the wrist-worn device when worn) such that the primary slits are generally along a width of a band of the wrist-worn device. In the implementation where strips of dielectric are provided in the gaps/spaces between the top/distal and bottom/proximal electrode layers, the strips of dielectric may be positioned transverse or perpendicular to the elongate slits and/or parallel with the proximal electrode strips. As used herein, the terms "proximal" and "distal" are to be taken as relative to the skin-engaging surface of the wearable device. For example, "distal" is to be understood as relatively close to the skin-engaging surface of device or toward the skin of the user. "Proximal" is to be understood as relatively further from the skin-engaging surface of the device or a direction away from the skin of the user when the device is coupled with the user. In some embodiments, a display may be provided that is on an outward-facing surface of the device and the sensor array may be provided on an inward-facing surface of the device.

In further embodiments, a sensor array may be provided where the top/distal layer and bottom/proximal layer of electrodes are independent or not shared with other nodes of the sensor array (e.g., separate squares or the like versus row/column shared electrode strips). Put in another way, the independent electrodes may form only part of one capacitive node, while shared electrodes may be part of multiple capacitive nodes. The dielectric layer disposed between the top and bottom electrodes may form pillars between the top and bottom independent electrodes such that the dielectric is disposed in the active area of the nodes of the sensor array. In alternative embodiments, the dielectric layer may have a configuration where the dielectric is disposed between the rows and columns of the independent electrodes such that air is primarily disposed between the top and bottom electrodes.

In some embodiments, the top layer of electrodes may include spaces that are formed between adjacent top electrodes to further decouple adjacent nodes. For example, the top layer of electrodes may protrude from a surrounding surface or the spaces between adjacent electrodes may be recessed to provide the space or air gap between adjacent top electrodes. The sensor arrays disclosed herein may allow for improved sensing resolution by decoupling of nodes.

In some embodiments, a wrist-worn device is provided. The device may be configured to be worn about a wrist of a user and may be further configured to measure a blood pressure of the user from an artery of the user. The wrist-worn device may include a sensor array comprising a plurality of capacitive nodes configured to couple with the skin of the user to measure the blood pressure of the user. The sensor array may include one or more distal electrodes positioned above a plurality of proximal electrodes. The one or more distal electrodes may be separated from the proximal electrodes by a gap. Capacitive nodes of the sensor array may be formed at laterally spaced apart locations where the one or more distal electrodes overlap with a proximal electrode. The distal surface of the laterally spaced apart capacitive nodes may protrude distally to form spaced apart protrusions of the sensor array. The spaced apart protrusions may decrease cross-talk between adjacent capacitive nodes of the sensor array.

In some embodiments, a flexible conductive layer, such as a conductive silicone, forms the distal electrode of each of the sensing nodes. The flexible conductive layer may be a skin contact layer of the sensor array. The plurality of proximal electrodes may be independent electrodes in some embodiments. Optionally, the plurality of proximal electrodes may be shared electrodes running parallel with one another.

A dielectric layer may be disposed in the gap between the distal electrode(s) and the plurality of proximal electrodes. The dielectric layer may include laterally spaced apart pillars. The laterally spaced apart pillars of the dielectric layer may be positioned at each of the capacitive nodes of the sensor array where the distal electrode overlaps with the proximal electrode. The pillars may support the distal electrode relative to the proximal electrode of each of the capacitive nodes of the sensor array. The laterally spaced apart pillars of the dielectric layer may further reduce cross-talk between adjacent capacitive nodes of the sensor array. In some embodiments, the laterally spaced apart pillars of the dielectric layer have circular cross-sections along a length of the pillars. In some embodiments, the laterally spaced apart pillars of the dielectric layer have rectangular cross-sections along a length of the pillars.

Optionally, the dielectric layer may include strips supporting the one or more distal electrodes relative to the plurality of proximal electrodes. The strips of the dielectric layer may be positioned in spaces between adjacent capacitive nodes.

In some embodiments, primary slits may be provided between adjacent capacitive nodes that extend in a direction of blood travel through the artery of the user when the wrist-worn device is worn about the wrist of the user. Secondary lateral slits may be provided that extend from the primary slits in a direction perpendicular to the primary slits or otherwise transverse (e.g., with 85% of normal to the primary slits). The secondary lateral slits may at least partially separate adjacent capacitive nodes.

The sensor array may include rows and columns of capacitive nodes and adjacent rows of the capacitive nodes of the sensor array may be staggered relative to adjacent rows (e.g., such that nodes are not aligned in uniform columns). Optionally, the sensor array may be curved. For example, the sensor array may have a radius of curvature between 12 mm and 20 mm.

The wrist-worn device may further comprise pins and a frame. Each of the pins may be operatively coupled with one of the capacitive nodes of the sensor array such that the pins push against a node of the capacitive sensor array. The pins may be restricted to movement in the proximal-distal direction by the frame (e.g., within 90% of normal to the sensor array).

In further aspects of the present disclosure, a wrist-worn device may be provided that is configured to be worn about a wrist of a user. The wrist-worn device may include a sensor array comprising a plurality of capacitive nodes configured to couple with the skin of the user to measure the blood pressure of the user. The sensor array may include a sheet of flexible conductive film, such as a conductive silicone layer, positioned above a plurality of spaced apart proximal electrodes by a gap. The capacitive nodes of the sensor array may be formed at laterally spaced apart locations where the conductive silicone overlaps with a proximal electrode. The sensor array may include rows and columns of capacitive nodes. Adjacent rows of the capacitive nodes of the sensor array may be staggered such that nodes are not aligned in uniform columns. The plurality of proximal electrodes may comprise individual electrodes (i.e., not shared electrodes). Optionally, the sensor array is curved with a radius of curvature between 12 mm and 20 mm.

The wrist-worn device may further include pins and a frame. Each of the pins may be coupled with one of the capacitive nodes of the sensor array. The pins may be restricted to movement in the proximal-distal direction by the frame (e.g., within 90% of normal to the sensor array).

Primary slits may be provided between adjacent capacitive nodes that extend in a direction of blood travel through the artery of the user when the wrist-worn device is worn about the wrist of the user (e.g., along a width of a device band or transverse to a longitudinal axis of the device). Secondary lateral slits may extend from the primary slits in a direction transverse or perpendicular to the primary slits— the secondary lateral slits may at least partially separate adjacent capacitive nodes.

A dielectric layer may be provided that is disposed in the gap between the sheet of flexible conductive film and the plurality of proximal electrodes. The dielectric layer may include laterally spaced apart pillars. The laterally spaced apart pillars of the dielectric layer may be positioned at each of the capacitive nodes of the sensor array where the conductive film overlaps with the proximal electrode. The pillars may support the conductive film relative to the proximal electrode of each of the capacitive nodes of the sensor array. The laterally spaced apart pillars of the dielectric layer may further reduce cross-talk between adjacent capacitive nodes of the sensor array.

The laterally spaced apart pillars of the dielectric layer may have circular cross-sections along a length of the pillars. The laterally spaced apart pillars of the dielectric layer may have rectangular cross-sections along a length of the pillars.

Optionally, the dielectric layer includes strips supporting the conductive film relative to the plurality of proximal electrodes. The strips of the dielectric layer may be positioned in spaces between adjacent capacitive nodes.

In further aspects, a wrist-worn device may be provided with a sensor array comprising a plurality of capacitive nodes configured to couple with the skin of the user to measure the blood pressure of the user. The sensor array may include one or more distal electrodes positioned above a plurality of proximal electrodes and separated by a gap. Capacitive nodes of the sensor array may be formed at laterally spaced apart locations where the one or more distal electrodes overlap with a proximal electrode. Primary slits may be provided between adjacent capacitive nodes that extend in a direction of blood travel through the artery of the user when the wrist-worn device is worn about the wrist of the user. In some embodiments, the primary slits may be transverse to a length or longitudinal axis of a band of the device or generally along a width of the band of the device. Secondary lateral slits may be provided that extend from the primary slits in a direction transverse or perpendicular to the primary slits. The secondary lateral slits may at least partially separate adjacent capacitive nodes.

The distal electrode(s) and/or proximal electrodes may be parallel shared electrode strips. The sensor array may be curved with a radius of curvature between 12 mm and 20 mm.

The wrist-worn device may further include pins and a frame. Each of the pins may be coupled with one of the capacitive nodes of the sensor array. The pins may be restricted to movement in the proximal-distal direction by the frame.

In further aspects, a wrist-worn device may be provided that includes a sensor array comprising a plurality of capacitive nodes configured to couple with the skin of the user to measure the blood pressure of the user. The sensor array may comprise one or more distal electrodes positioned above a plurality of proximal electrodes and separated by a gap. The capacitive nodes of the sensor array may be formed at laterally spaced apart locations where a distal electrode overlaps with a proximal electrode. The sensor array may be curved and may have a radius of curvature between 12 mm and 20 mm.

In some aspects, a wrist-worn device may be provided that is configured to measure pressure signals where the wrist-worn device includes a sensor array comprising a proximal layer, a distal layer, and a dielectric layer supporting the proximal layer relative to the distal layer. The proximal layer may include one or more proximal electrodes. The distal layer may include one or more distal electrodes. Capacitive nodes of the sensor array may be formed at locations where a distal electrode overlaps with a proximal electrode. The proximal layer may include a plurality of cantilevered fingers which are each separated from adjacent fingers by a slit.

In some embodiments, each of the plurality of cantilevered fingers may be parallel with one another. Optionally, stiffeners may be coupled with a proximal surface of each of the plurality of cantilevered fingers.

In certain embodiments, the fingers may be in a folded configuration. An actuator (e.g., fluid bladder or the like) may be sandwiched by the folded plurality of fingers of the proximal layer. Stiffeners may be coupled with a proximal surface of the plurality of fingers that is adjacent to a free end of the plurality of fingers. The actuator may be coupled with a proximal surface of stiffeners in some embodiments.

Embodiments of the disclosure covered by this patent are defined by the claims below, not this summary. This summary is a high-level overview of various aspects of the disclosure and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

The disclosure will be better understood on reading the following description and examining the figures that accompany it. These figures are provided by way of illustration only and are in no way limiting on the disclosure.

DETAILED DESCRIPTION

Figure 1:
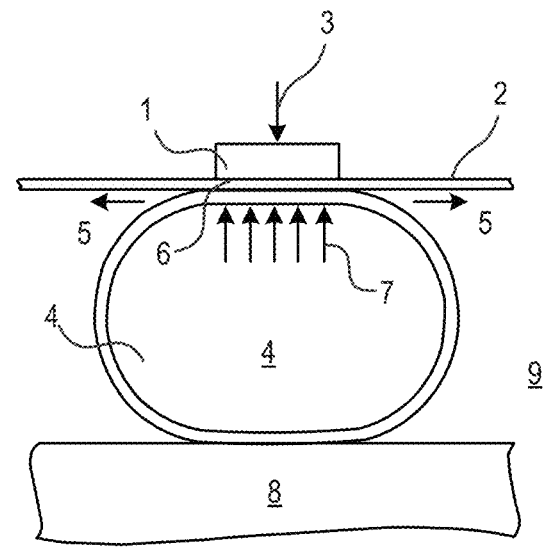
FIG. 1 shows a prior art method of applanation tonometry.

The present disclosure generally relates to pressure measurements which may be helpful in measuring one or more user parameters. In some embodiments, methods and devices for measuring a mean arterial pressure and/or for monitoring blood pressure changes of a user are provided. In particular, the present disclosure provides devices, system, and methods for improved sensing by decoupling nodes of the sensor array so as to provide improved signal resolution and hence more accurate blood pressure measurements. The decoupling of nodes of the sensor array helps reduce crosstalk between adjacent nodes. This may help identify one or more nodes of the sensor array which are better positioned adjacent a target artery for measuring a blood pressure or heart beat pulse of the user.

A person's blood pressure is a continuously changing vital parameter. As a result, blood pressure measurements during intermittent visits to a physician may be insufficient to detect some forms of hypertension. For example, hypertension can occur in a pattern that evades detection during a visit to the physician's office. Common hypertension patterns include white coat hypertension (elevated only during a limited morning period of time), borderline hypertension (fluctuating above and below definitional levels over time), nocturnal hypertension (elevated only during sleeping hours), isolated systolic hypertension (elevated systolic pressure with non-elevated diastolic pressure), and isolated diastolic hypertension (elevated diastolic pressure with non-elevated systolic pressure). To detect such hypertension patterns, it may be beneficial to perform additional blood pressure measurements over time to obtain a more complete view of a person's blood pressure pattern and features. Although continuous measurement of blood pressure can be achieved by invasive means, for example, via an intra-arterial pressure sensing catheter, noninvasive blood pressure measurement approaches are more preferable.

Current noninvasive blood pressure measurement approaches include ambulatory and home blood pressure measurement strategies. These strategies provide a more complete view of a person's blood pressure characteristics and are often employed in recommended situations. Ambulatory blood pressure measurement is performed while the person performs daily life activities. Currently, ambulatory blood pressure measurements are typically performed every 20 to 30 minutes using brachial oscillometric blood pressure measurement cuffs. Ambulatory blood pressure measurement may be recommended where there is large variability in in-office blood pressure measurements, where a high in-office blood pressure measurement is measured in a person with otherwise low cardiovascular risk, when in-office and home blood pressure measurements vary, where resistance to drug treatment of high-blood pressure is noted or suspected, where hypotensive episodes are suspected, or where pre-eclampsia is suspected in pregnant women. Home blood pressure measurement includes isolated self-measurements performed by a person at home. Home blood pressure measurements may be recommended where information is desired regarding the effectiveness of blood pressure lowering medication over one or more dose-to-dose intervals and/or where doubt exists as to the reliability of ambulatory blood pressure measurement.

Current ambulatory and home blood pressure measurement approaches, however, fail to provide continuous measurement of blood pressure. Additionally, when an oscillometric blood pressure measurement cuff is used to monitor a person's blood pressure when sleeping, the intermittent inflation and deflation of the cuff can disturb the person's sleeping pattern, thereby potentially changing the person's sleeping blood pressure. Thus, convenient and effective approaches for noninvasive continuous measurement of blood pressure remain of interest.

In applanation tonometry, the pressure in a superficial artery with sufficient bony support, such as the radial artery, may be accurately recorded during an applanation sweep when the transmural pressure equals zero. An applanation sweep refers to a time period during which pressure over the artery is varied from overcompression to undercompression or vice versa. At the onset of a decreasing applanation sweep, the artery is overcompressed into an occluded state, so that pressure pulses are not recorded. At the end of the sweep, the artery is undercompressed, so that minimum amplitude pressure pulses are recorded. Within the sweep, it is assumed that an applanation occurs where the arterial wall is flattened and transmural pressure turns to zero, and the arterial pressure is perpendicular to the surface and is the only pressure detected by a tonometer sensor.

FIG. 1 illustrates a method of measuring blood pressure using applanation tonometry. Here, a pressure transducer 1 is urged against the skin 2 of a user with an applanation force 3. The applanation force 3 and pressure transducer 1 applanate the target artery 4 such that the arterial wall tension 5 is parallel to the pressure transducer surface 6 and the arterial pressure 7 is perpendicular to the surface 6. Where the target artery 4 is applanated in such a manner, the arterial pressure may be measured by transducer 1. The target artery 4 may be supported by bone 8 and adjacent muscle 9. The target artery 4 may be the radial artery of the user and the bone 8 may be the radial bone.

Figure 2:
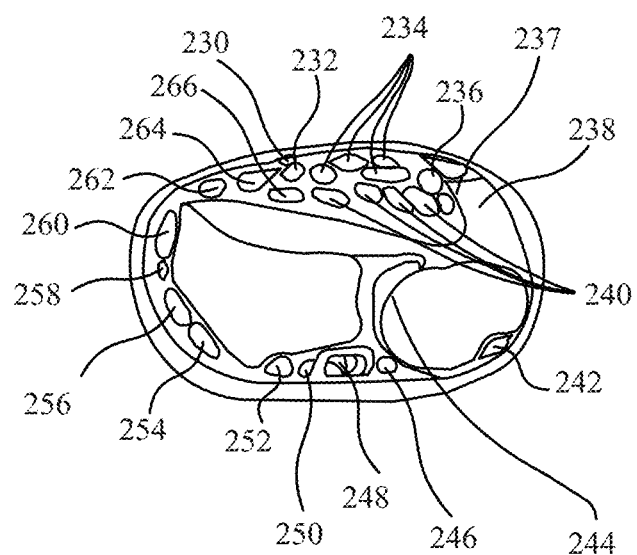
FIG. 2 shows the cross section of a wrist.

FIG. 2 illustrates an exemplary cross-section of a wrist which may include: palmaris longus tendon 230, median nerve 232, flexor dig. sublimis 234, ulnar artery 236, ulnar nerve 237, flexor carp. uln. 238, flex. dig. profundus 240, ext. carp. uln. 242, distal radio-unlar artic. 244, ext. dig. quinti prop. 246, ext. dig. commun. 248, ext. indicis. prop. 250, ext. poll. long. 252, ext. carp. rad. brev. 254, ext. carp. rad. long. 256, ext poll brev. 258, abd. poll. long. 260, radial artery 262, flex. carp. rad. 264, and flex. poll. long. 266. As mentioned above, the radial artery 262 is generally targeted in arterial applanation tonometry given its position adjacent the radial bone (radius).

As mentioned above, the radial artery is generally targeted in arterial applanation tonometry given its position adjacent the radial bone (radius). However, finding an ideal or preferred location for applanation of the radial artery can be difficult given its relative size. Compounding this problem is the fact that human anatomy varies from person to person and may change based on a person's height, weight, gender, etc. Accordingly, targeting the radial artery and identifying a preferred applanation location and orientation can be a challenge.

Due to anatomical constrains and variations in sensor placement, it may be difficult to obtain an accurate pressure signal from a target artery. Some blood pressure measurement devices and methods have relied on bulky wrist harnesses to orient a user's wrist in a preferred orientation to help with sensor placement, however such devices and methods are not practical for daily use by the general public. Additionally, the use of a sensor array to increase the chance that at least one the sensors or sensing nodes of the sensor array is properly placed relative to the target artery comes with its own challenges.

Figure 3:
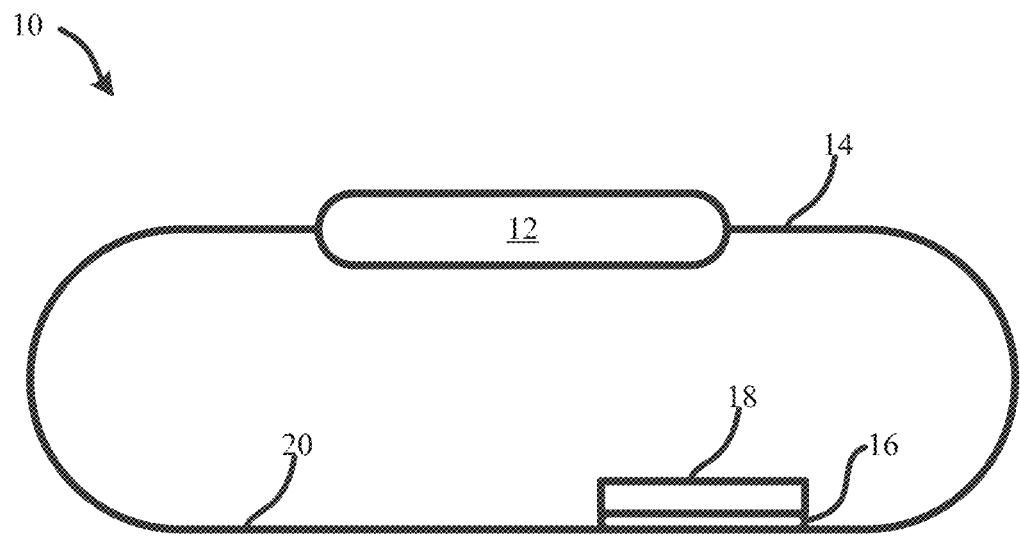
FIG. 3 illustrates an exemplary device according to some embodiments of the present disclosure.

FIG. 3 illustrates an exemplary device 10 according to some embodiments of the present disclosure for measuring pressure of a user. Device 10 includes a device body 12 and a device band 14. An actuator 16 may be supported by device band 14. A sensor array 18 may be coupled with the actuator 16.

In many embodiments, the device 10 may be a wrist-worn device (e.g., an electronic watch or the like). The device body 12 may house a data processor of device 10. The device body 12 may also provide a user interface for receiving user input and outputting information to the user (e.g., through a display or integrated audio device or the like). The device band 14 may comprise one or more flexible bands configured to couple the device 10 to the user (e.g., to the user's wrists). The device body 12 and device band 14 may have an inward-facing skin-engaging surface 20 opposite an outward-facing surface of the device. In some embodiments, it may be preferable if the device 10 does not require a harness for positioning the user's wrist in a particular manner when measuring a blood pressure of the user. Avoiding a wrist harness may decrease the bulkiness of the device 10 and may increase adoption of the device 10 for blood pressure measurements by general consumers.

The actuator 16 may be a linear actuator for driving the sensor array 18 into the skin of the user. For example, the actuator 16 may urge the sensor array 18 against a target artery of the user to conduct an applanation sweep for applanation tonometry. The actuator 16 may be a fluid or air bladder or the like, driven by a pump. The actuator may also be a linear electromagnetic motor. The actuator may be a rotary electromagnetic motor driving a lead screw, or cam, or gears to provide the force and displacement for applanation. The actuator may be driven by piezoelectric, electroactive polymer, or shape memory alloy materials. The sensor array 18 may be an array of capacitive nodes, details of which are described further below. The sensor array 18 may be coupled with the data processor housed in device body 12 or may be operatively coupled with a separate processor that is coupled with the device band 14. Alternatively, there may be control/processing circuitry in the band 14, but may use the processor of the device body 12.

Figure 4:
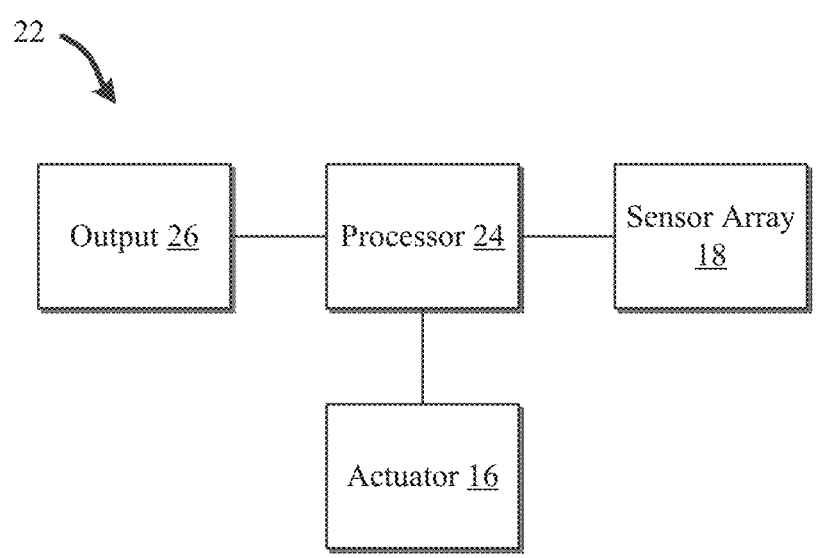
FIG. 4 illustrates an exemplary system according to some embodiments of the present disclosure.

FIG. 4 illustrates an exemplary system diagram 22 of the device 10. The device 10 may include a processor 24. The processor 24 may be coupled with and may control actuation of the actuator 16. Additionally, the processor 24 may be further coupled with the sensor array 18. The processor 24 may be configured to receive signals from each of the nodes of the sensor array 18 and may be further configured to process the signals to determine a pressure sensed by each of the nodes of the array 18. The processor 24 may detect and compute a pulse rate of the user and/or a blood pressure measurement of the user based on the one or more signals from the sensor array 18. The processor 24 may then output the measured attribute to the user in a manner perceptible to the user via output 26. The output 26, may be an audio output, a display, or the like. In some embodiments, the data may be wirelessly communicated to another electronic device, optionally associated with the user, for further processing and/or output to the user. Accordingly, in some instances, the information may be transmitted to another device (e.g., user device or physician device, etc.) where the information is accessed.

Figure 5:
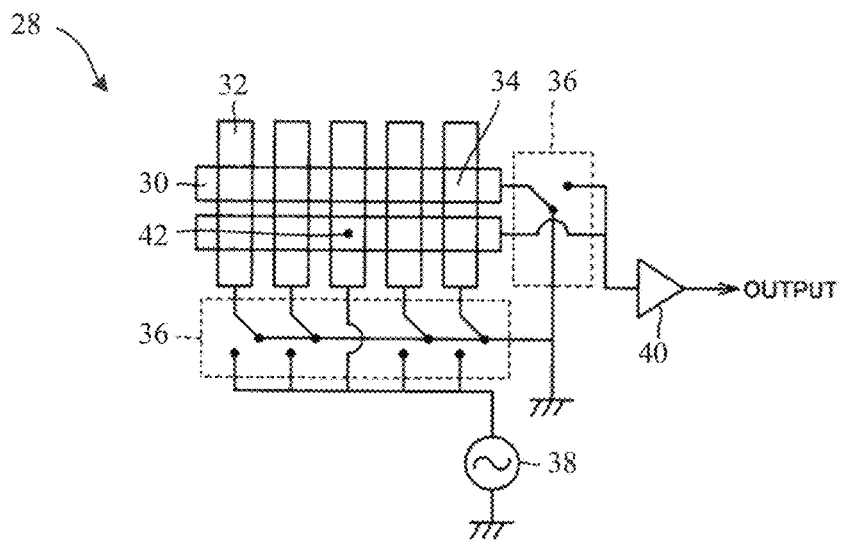
FIG. 5 illustrates an exemplary device schematic according to some embodiments of the present disclosure.

FIG. 5 illustrates an exemplary sensor array 28 according to some embodiments of the present disclosure. The array 28 includes bottom/proximal electrodes 30 and top electrodes 32. Bottom electrodes 30 may be formed of a plurality of conductive strips that are arranged side by side in rows to extend substantially linearly. Top/distal electrodes 32 may be formed of a plurality of conductive strips that are arranged side by side in columns to extend substantially linearly in a direction orthogonal to bottom electrodes 30. The conductive strips may be a conductive metal, which in some instances may be copper.

At each of the intersections of bottom electrodes 30 and upper electrodes 32 arranged in rows and columns, a part of lower electrode 30 and a part of upper electrode 32 face each other with a prescribed distance therebetween. In this manner, capacitive nodes 34 are formed at the intersections and serve as the sensing nodes of the sensor array 28.

Capacitive nodes 34 may be aligned in the form of an array when the pressure detecting portion is seen along the distal-proximal direction. Each capacitive node 34 has its capacitance changed as pressure is applied to upper electrode 32 or lower electrode 30 which causes them to deflect in the direction decreasing the distance therebetween.

With lower electrodes 30 and upper electrodes 32 arranged in rows and columns, respectively, a circuit configuration may be provided where one electrode, e.g., the lower electrodes 30 or the upper electrodes 32, may be connected via a multiplexer 36 to a power source 38 and the other electrodes, e.g., the upper electrodes 32 or the lower electrodes 30, are connected via multiplexer 36 to a detector 40. With this configuration, when a particular lower electrode 30 and a particular upper electrode 32 are selected by multiplexer 36, capacitance of a specific one of the capacitive nodes 34 arranged in the array form can be obtained via detector 40. For example, in FIG. 5, when lower electrode 30 on the second row from the top and upper electrode 32 on the third column from the left are selected, the capacitance of the capacitive node denoted by a reference 42 is output. Thus, it is possible to measure the pressure at a given position on the sensing surface of sensor array 28. The electrodes connected to the drive signal (i.e., power source 38) may be referred to as "drive" electrodes while the electrodes connected to the sensor (i.e., multiplexer 36) may be referred to as "sense" electrodes. While FIG. 5 illustrates a configuration with a single drive source and a single sensor detector, it should be understood that there could be multiple drive sources and/or multiple detectors. Multiple drive sources may allow multiple drive electrodes to be stimulated simultaneously (and thus multiple nodes along a single sense electrode to be measured simultaneously). In these instances, each drive source may stimulate with a different frequency, and the signal sensed from the sense electrode may be demodulated to determine the signal from each node of the sensor array. Multiple detectors may allow nodes across different sense electrodes to be sensed simultaneously.

While the sensor array 28 is illustrated as having two parallel lower electrode strips 30 and five parallel upper strips 32 to provide a 2×5 array of capacitive nodes 34, it should be understood that the sensor array 28 may have other configurations. For example, a 5×5 array, 6×6 array, 6×9 array, or the like may be provided. In some embodiments, the sensor array may be dimensioned to sense pressures from a 10 mm×10 mm area. The capacitive nodes may have a sensing area of approximately 1 mm by 1 mm.

Figure 6:
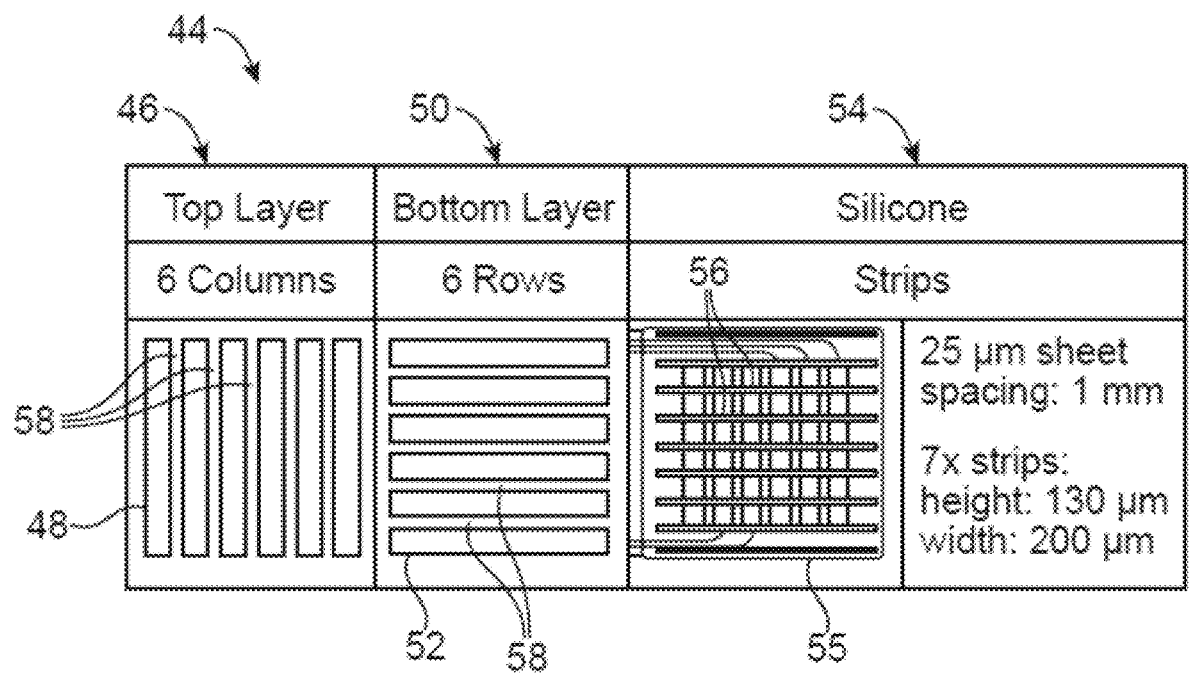
FIG. 6 illustrates components of an exemplary capacitive sensor array according to some embodiments of the present disclosure.

For example, FIG. 6 illustrates components of an exemplary 6×6 sensor array 44 that may be used with device 10 according to some embodiments of the present disclosure. The sensor array 44 is formed by a top layer 46 of six columns of electrode strips 48 and a bottom layer 50 of six rows of electrode strips 52. The strips of electrodes may have a width between 0.5-1.5 mm, preferably 1 mm. A dielectric layer 54 may be provided between the top layer 46 and the bottom layer 50. The dielectric layer 54 may include a sheet 55 of dielectric material and strips 56 of dielectric material. In some embodiments, the sheet 55 of dielectric material may have a thickness between 10-50 µm, preferably about 25 µm. The strips 56 of dielectric material may run in the lateral gaps 58 between one of the rows or columns of the electrode strips 48, 52. The lateral gaps 58 may have a width between 150-400 µm and may be filled with a different dielectric material other than air (e.g., a softer dielectric than the dielectric strips 56 or a liquid/gel dielectric). The dielectric strips 56 may act as a spacer member between the top layer 46 and the bottom layer 50 and support the top layer 46 relative to the bottom layer 50 to help maintain a prescribed distance between the two electrode layers 46, 50. The strips 56 of dielectric material may have a 1 mm spacing between adjacent strips 56. The strips 56 may have a height of approximately 130 µm and a width of approximately 200 µm. While illustrated with a single continuous strips 56 in lateral gaps 58, other embodiments may utilize a series of strips 56 orientated end-to-end with optional spacing therebetween. In some embodiments the dielectric material may be silicone.

Figure 7:
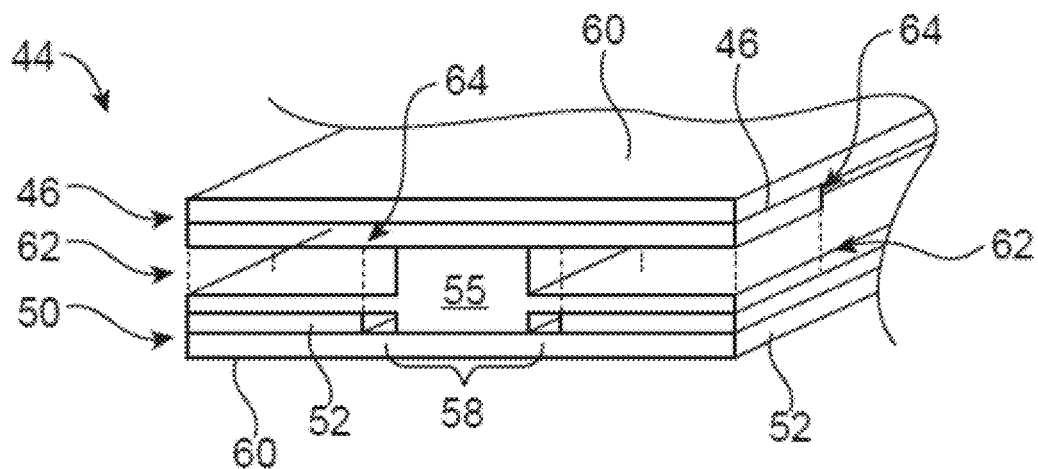
FIG. 7 illustrates an isometric view of a portion of an exemplary capacitive sensor array according to some embodiments of the present disclosure.

FIG. 7 illustrates a schematic diagram of a portion of the array 44 as assembled. As illustrated in FIG. 7, the top and bottom layers 46, 50 may be coupled with a backing material 60. The backing material 60 may be a polyimide film or the like. Further, an air gap may be provided in the active area 62 of a capacitive node 64 formed by the electrode strips 48, 52. Further as illustrated, the dielectric strip 55 is disposed in the gap 58 between adjacent bottom electrode strips 52. In some embodiments, utilizing strips 55, the active area 62 may be primarily filled with air which may increase the deflection/sensitivity of the capacitive nodes to changes in pressure.

Figure 8:
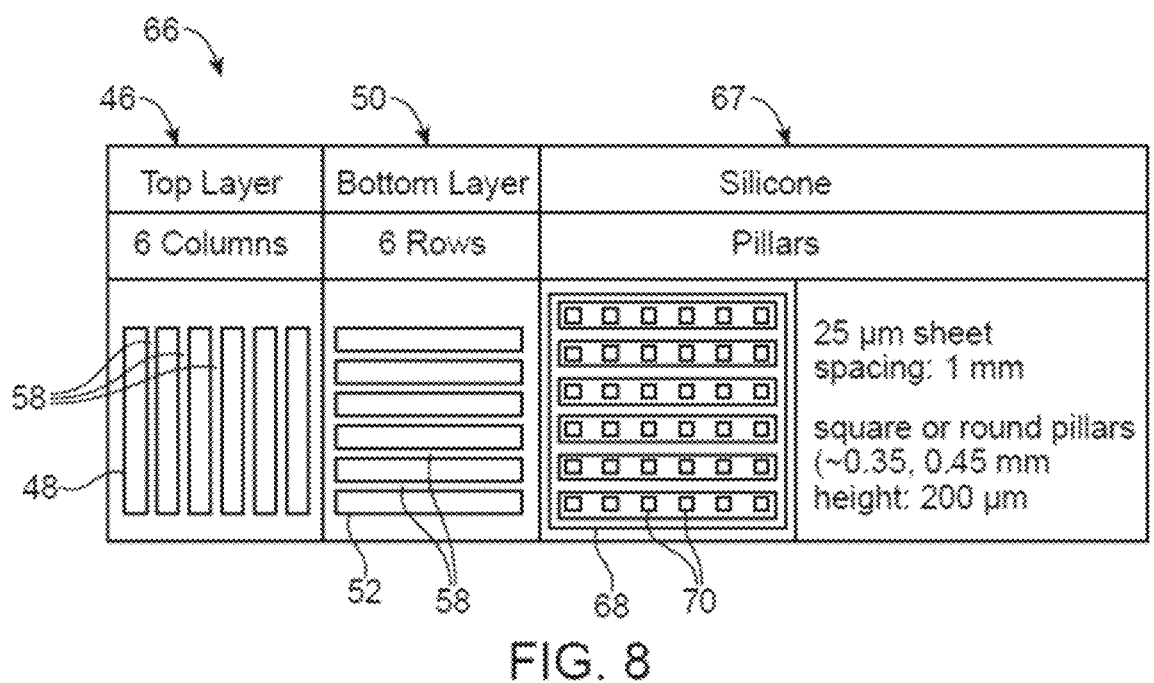
FIG. 8 illustrates components of another exemplary capacitive sensor array according to some embodiments of the present disclosure.

FIG. 8 illustrates components of another exemplary capacitive sensor array 66 that may be used with device 10 according to some embodiments of the present disclosure. Similar to array 44, capacitive sensor array 66 may include a top layer 46 of six columns of electrode strips 48 and a bottom layer 50 of six rows of electrode strips 52. Each of the strips 48, 52 may be separated from adjacent strips by a gap 58. A dielectric layer 67 may be provided between the top layer 46 and the bottom layer 50. The dielectric layer 67 may include a sheet 68 of dielectric material and pillars 70 of dielectric material. In some embodiments, the sheet 68 of dielectric material may have a thickness between 10-50 µm, preferably about 25 µm. The pillars 70 of dielectric material may be disposed at the intersection of the electrode strips 48 of the top layer 46 with the electrode strips 52 of the bottom layer 50. The dielectric pillars 70 may act as a spacer member between the top layer 46 and the bottom layer 50 and support the top layer 46 relative to the bottom layer 50 to help maintain a prescribed distance between the two electrode layers 46, 50. The pillars 70 of dielectric material may have a height of approximately 100-300 µm. The pillars 70 may have a rectangular cross-section or a circular cross-section or the like. A diameter or width of the pillars 70 may range from approximately 200-550 µm, preferably about 350-450 µm.

Figure 9:
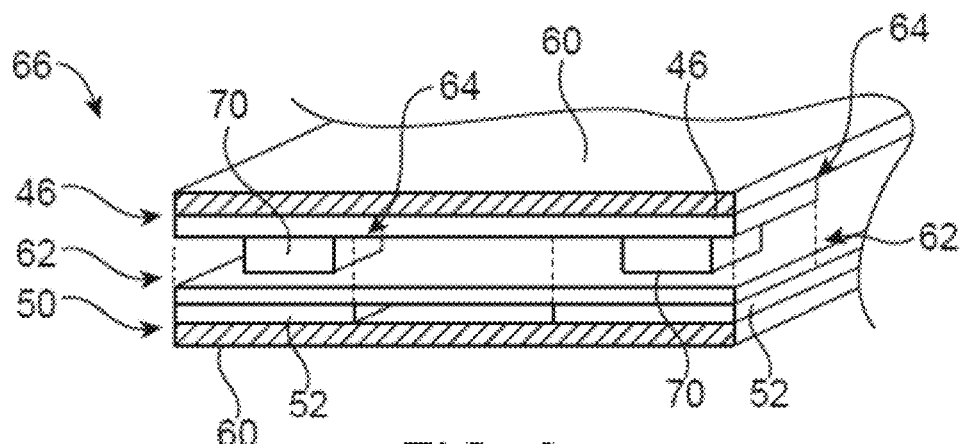
FIG. 9 illustrates an isometric view of a portion of an exemplary capacitive sensor array according to some embodiments of the present disclosure.

FIG. 9 illustrates an isometric view of a portion of an exemplary capacitive sensor array 66 as assembled, according to some embodiments of the present disclosure. As illustrated in FIG. 9, the top and bottom layers 46, 50 may be coupled with a backing material 60. The backing material 60 may be a polyimide film or the like. Further, pillars 70 may be provided in the active area 62 of a capacitive node 64 formed by the electrode strips 48, 52.

Figure 10:
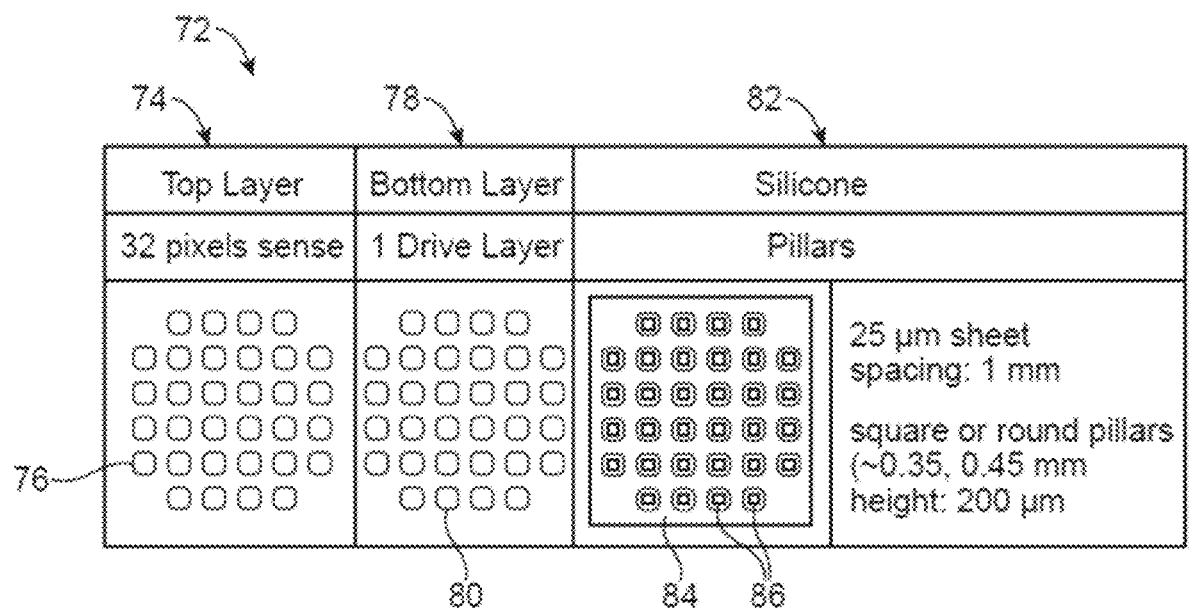
FIG. 10 illustrates components of yet another exemplary capacitive sensor array according to some embodiments of the present disclosure.

FIG. 10 illustrates components of yet another exemplary capacitive sensor array 72 that may be used with device 10 according to some embodiments of the present disclosure. The capacitive sensor array 72 may include a top layer 74 of independent electrodes 76 that are laterally spaced from one another. In some embodiments thirty two electrodes 76 may be provided. The electrodes 76 may be arranged in a symmetrical array with a top row of four electrodes; the second-fifth rows including six electrodes; and a sixth row including four electrodes. The electrodes 76 may be sense electrodes. A bottom layer 78 may also include independent electrodes 80. In some embodiments the bottom layer 78 includes thirty two electrodes 80, each of which correspond to one of the sense electrodes 76 to form a plurality of capacitive nodes. Accordingly, the electrodes 80 may also be arranged in a symmetrical array with a top row of four electrodes; the second-fifth rows including six electrodes; and a sixth row including four electrodes. The electrodes 80 may be driven separately or, optionally, the electrodes 80 may all be driven together to form a drive layer of the capacitive sensor array 72. It should be understood that the configuration may be swapped such that the bottom electrodes may be sensed (separately or together) and the top electrodes may be driven (separately or together). A middle layer 82 of dielectric material may be provided to provide the spacing between the top layer 74 and the bottom layer 78. The dielectric layer 82 may include a sheet 84 of dielectric material and pillars 86 of dielectric material. Similar to the embodiments described above, the sheet 84 may have a thickness between 10-50 µm, preferably about 25 µm. The pillars 86 of dielectric material may be spaced apart from one another by approximately 1 mm so as to be disposed at the capacitive nodes formed by each of the electrodes 76, 80. The dielectric pillars 86 may act as a spacer member between the top layer 74 and the bottom layer 78 and may support the top layer 74 relative to the bottom layer 78 to help maintain a prescribed distance between the two electrode layers 74, 78. The pillars 86 of dielectric material may have a height of approximately 100-300 µm, preferably 200 µm. The pillars 86 may have a rectangular cross-section or a circular cross-section or the like. A diameter or width of the pillars 86 may range from approximately 200-550 µm, preferably about 350-450 µm. While the sensor arrays are illustrated as forming uniform arrays of nodes, it should be understood that the capacitive nodes may be staggered in some embodiments or otherwise offset from one another such that the nodes do not form uniform rows and/or columns.

Figure 11:
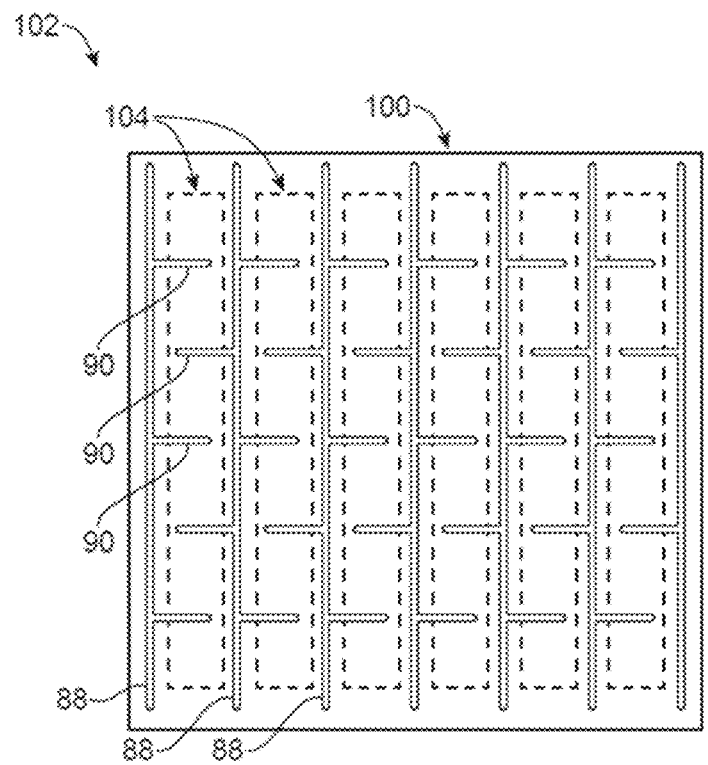
FIG. 11 illustrates primary and secondary lateral slits in a backing material of a capacitive sensor array according to some embodiments of the present disclosure.

In some embodiments, the electrode backing material (e.g., backing material 60) may be a relatively stiff material and may introduce some cross-talk between adjacent nodes. For example, deformation of the backing material at one point may be detected at adjacent areas. Accordingly, in some embodiments, slits in the backing material may be provided (e.g., via laser cutting or the like) to reduce this coupling introduced by the backing material. The slits may decrease mechanical coupling across the slit. For example, FIG. 11 illustrates primary slits 88 and secondary lateral slits 90 in a backing material 100 of a capacitive sensor array 102 according to some embodiments of the present disclosure. As illustrated, the backing film 100 may be cut to include primary slits 88 in the film 100 between the parallel strips of electrodes 104 so as to provide decoupling between the strips of electrodes 104. Additionally lateral slits 90 may be cut to extend from the primary slits 88 to increase decoupling along the electrode strips 104. In some embodiments, the lateral slits 90 may be staggered such that adjacent lateral slits 90 extend in an opposite direction from an adjacent primary slit 88. In some embodiments, the wrist-worn device may align the primary slits 88 along the length of the user's arm such that the distal/top electrode strips 104 are generally parallel to the radial artery of the user or aligned with the length of the user's arm. In the implementation where strips of dielectric are provided in the gaps/spaces between the top/distal and bottom/proximal electrode layers, the strips may be positioned transverse or perpendicular to the elongate slits 88 and parallel with the proximal electrode strips. Alternatively, the strips of dielectric may be positioned parallel to the elongate slits 88 and transverse or perpendicular to the proximal electrode strips. In some embodiments, the lateral slits 90 do not extend across the entire width of the electrode 104. In other embodiments, a lateral slit 90 may extend across the entire width of the electrode 104 and may join adjacent primary slits 88.

Figure 12:
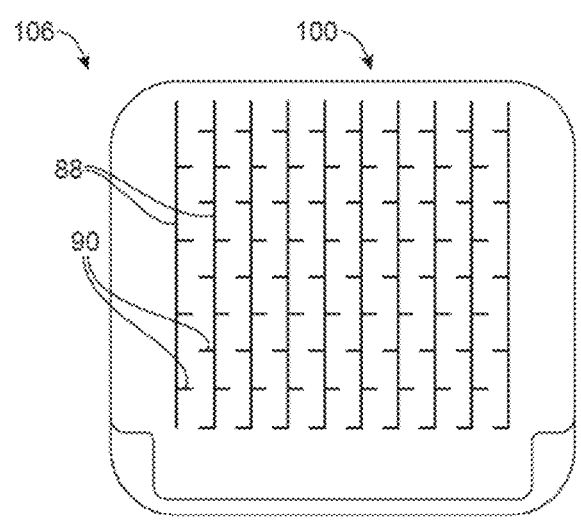
FIG. 12 illustrates primary and secondary lateral slits in a backing material of another capacitive sensor array according to some embodiments of the present disclosure.

While illustrated with six electrodes 104, it should be understood that the slits 88, 90 may be provided to sensor arrays having alternative configurations. For example, FIG. 12 illustrates primary 88 and secondary lateral slits 90 in a backing material 100 of another capacitive sensor array 106 according to some embodiments of the present disclosure. The capacitive sensor array 106 may have a 9×6 or 9×9 array of capacitive nodes for example. Additionally, it should be understood that the slits 88, 90 in the backing material may be utilized with any of the embodiments described above with reference to FIGS. 3-10 and below. For example, capacitive sensor arrays utilizing strips of electrodes and strips of dielectric may also take advantage of the slits in the backing material. Similarly, capacitive sensor arrays utilizing strips of electrodes and pillars of dielectric may also benefit from the slits in the backing material. Embodiments utilizing independent electrodes with independent drive electrodes may also benefit from one or more slits in the backing material between adjacent capacitive nodes.

Figure 13:
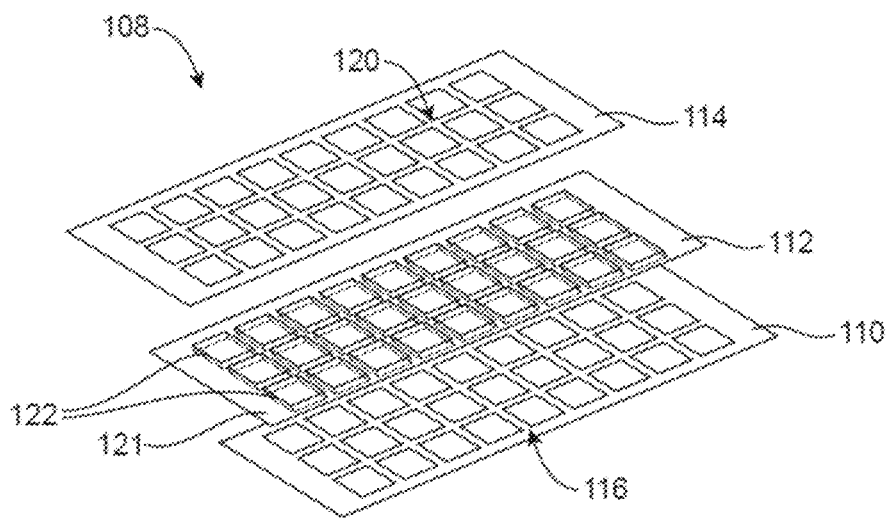
FIG. 13 illustrates yet another capacitive sensor array according to some embodiments of the present disclosure.
Figure 14:
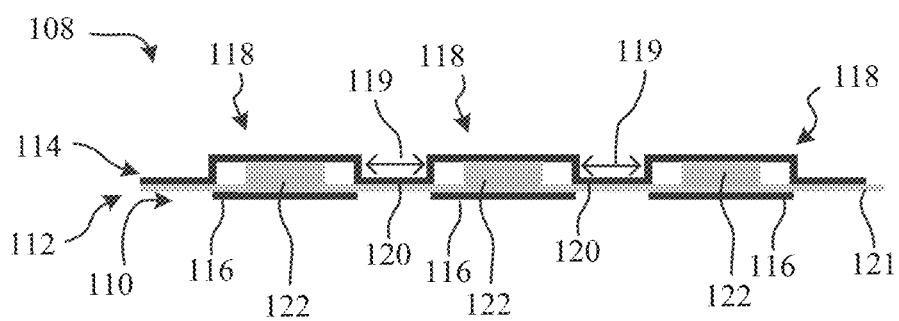
FIG. 14 illustrates a cross-sectional view of an exemplary capacitive sensor array according to some embodiments of the present disclosure.

FIG. 13 illustrates yet another capacitive sensor array 108 that may be used with device 10 according to some embodiments of the present disclosure. The capacitive sensor array 108 includes a bottom layer 110, a middle layer 112, and a top layer 114. The bottom layer 110 may include an array of independent bottom electrodes 116 (not shared electrodes/electrodes that only form part of a single capacitive node) that are laterally spaced apart. The bottom electrodes 116 may form a 3×9 array, although other array sizes are possible. The electrodes 116 may be a conductive material. In some embodiments, the electrodes 116 may be a conductive metal such as a copper material or the like. The top layer 114 may comprise a sheet of flexible conductive material. In some embodiments the top layer 114 may be conductive silicone. The top layer 114 may form a top shared electrode which cooperates with each of the bottom electrodes 116 to form a plurality of capacitive nodes 118 of the sensor array 108. In some embodiments, the top layer 114 at each of the nodes 118 may be raised or protruded from a surrounding surface of the top layer 114 as illustrated in the cross-sectional view provided by FIG. 14. Accordingly, in some embodiments, lateral air spaces or gaps 119 may be formed between the top layer 114 of adjacent nodes 118 that may further decouple adjacent capacitive nodes 118. In some embodiments, the interconnecting material 120 between the nodes 118 may be thin to increase flexibility at the interconnections between the nodes 118 so as to increase mechanical decoupling between adjacent nodes 118. The interconnecting material 120 may have a thickness between 25 µm and 500 µm. Additionally, the slits described above may be used to increase decoupling between adjacent nodes 118. For example, the slits may be provided in the sheet of flexible conductive material 114. Primary slits may be provided between adjacent nodes 118 of the array 108. Lateral slits may also extend from the primary slits and may be staggered to at least partially decouple adjacent nodes. The middle layer 112, may be a dielectric material such as silicone. The middle layer 112 may include a sheet 121 and an array of spaced apart pillars 122 that correspond to the capacitive nodes 118 of the sensor array 108. Pillars 122 may support the top layer 114 relative to the bottom layer 116 and bottom electrodes 116. The pillars 122 may be disposed in the active area of the nodes 118 as illustrated in the exemplary cross-sectional view of FIG. 14. The spaced apart pillars 122 may further decouple adjacent capacitive nodes 118 of the array 108.

Figure 15:
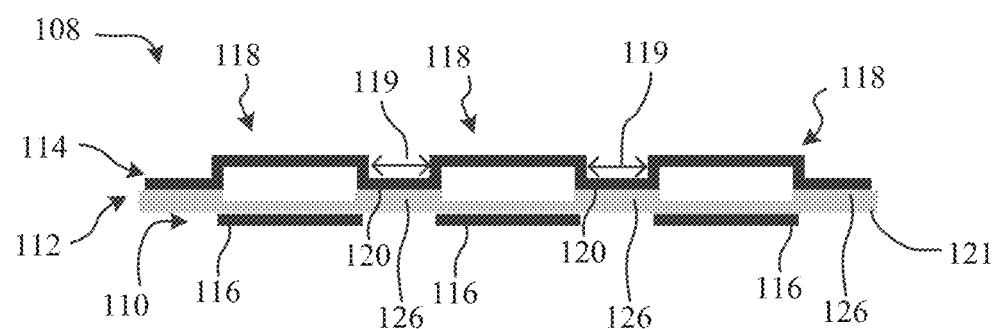
FIG. 15 illustrates a cross-sectional view of an alternative exemplary capacitive sensor array according to some embodiments of the present disclosure.

In alternative embodiments, the middle layer 112 may support the top layer 114 relative to the bottom layer 110 with strips 126 at locations between adjacent electrodes 116 of the array 108 as illustrated in FIG. 15. The strips 126 may couple with the interconnecting material 120 between electrodes 118. It should be understood that strips 126 may run between columns of the array and/or between rows of the array 108. With such a configuration, the capacitive nodes 118 may be more sensitive to pressure changes as air is primarily disposed in the active area of the nodes 118. While the array 108 is illustrated and described as protruding the top layer 114 at each of the nodes 118 such that gaps 119 are formed between adjacent nodes 118, it should be understood that other embodiments of the sensor array may not have the top layer 114 at each of the nodes 118 protruded from an adjacent surface.

Figure 16:
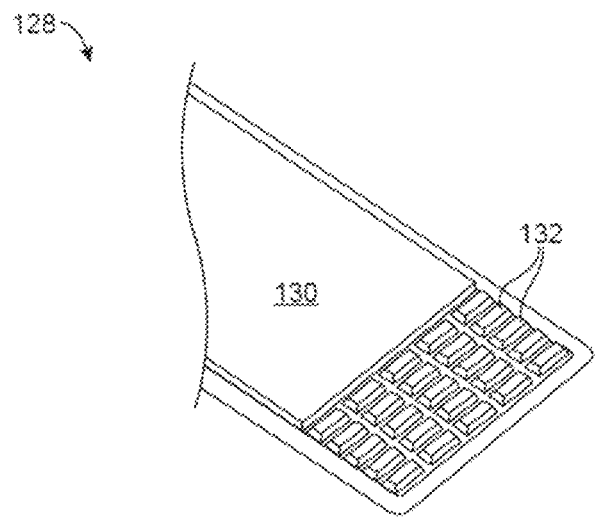
FIG. 16 illustrates another capacitive sensor array according to some embodiments of the present disclosure.
Figure 17:
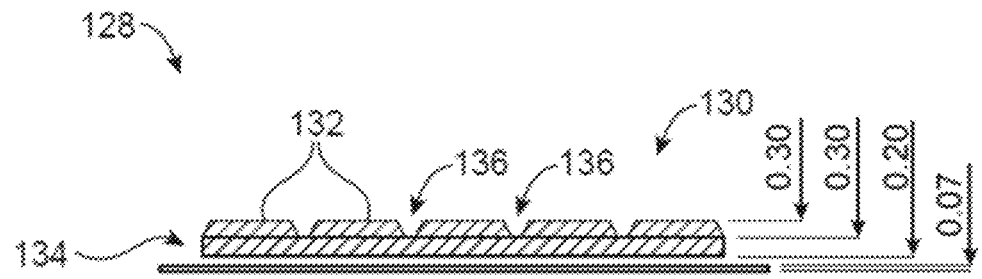
FIG. 17 illustrates a side view of the capacitive sensor array of FIG. 16.

FIG. 16 and FIG. 17 illustrate another capacitive sensor array 128 that may be used with device 10 according to some embodiments of the present disclosure. FIG. 17 illustrates a side view of the capacitive sensor array 128 of FIG. 16. The capacitive sensor array includes a top layer 130 comprising a conductive silicone. The top layer 130 forms top electrodes 132 of an array of capacitive nodes. The capacitive nodes form a 5×5 array of capacitive nodes. The bottom layer 134 includes independent bottom electrodes (not shown) corresponding to the top electrodes 132 of the top layer 130. As illustrated in FIG. 17, the top electrodes 132 may be separated by wedge shaped gaps 136 to decouple adjacent nodes. The top layer may have a thickness of 0.3 mm.

Figure 18:
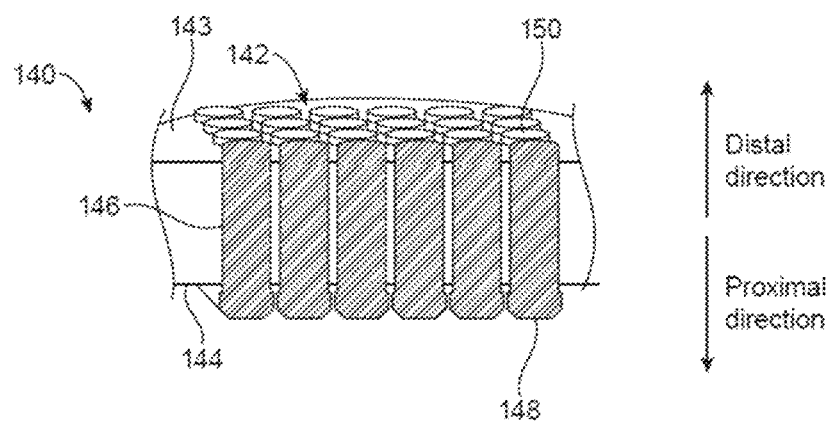
FIG. 18 illustrates a cross-sectional view of a frame and pin component that may be used with embodiments of the present disclosure.
Figure 19:
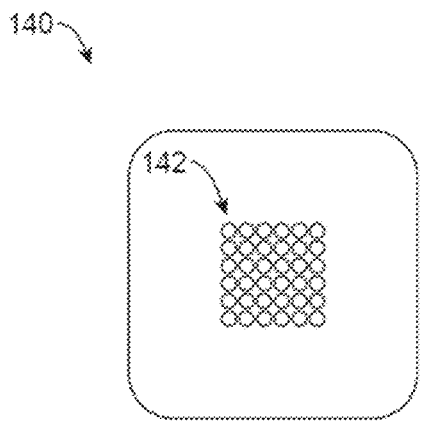
FIG. 19 illustrates a top view of the frame and pin component of FIG. 19.
Figure 20:
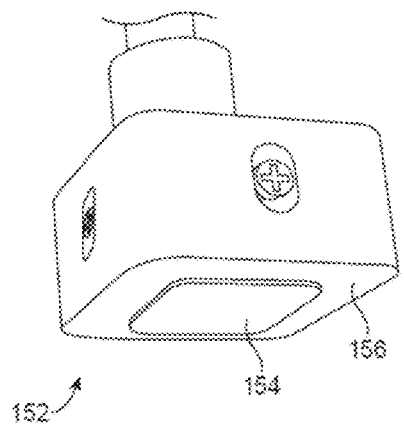
FIG. 20 illustrates a capacitive sensor array protruding from an adjacent contact surface according to some embodiments of the present disclosure.

FIG. 18 illustrates a cross-sectional view of a frame 140 and pin 142 component that may be used with device 10 to further decouple adjacent nodes of the sensor arrays described herein. FIG. 20 illustrates a top view of the frame 140 and pin 142 component of FIG. 19. The frame 140 may have a top surface 143, a bottom surface 144, and an array of channels 146 extending between the top surface 143 and the bottom surface 144. The pins 142 may be disposed in the channels 146 of the frame 140. The pins may have an elongate body having a proximal end 148 and a distal end 150. The elongate body may have a cross-section generally matching the channels 146 of the frame 140 and a length of the elongate body of the pin 142 may be greater than a length of the channels 146 such that the distal portion 150 of the pins 142 protrude from the top surface 143 of the frame 140. In some embodiments, the frame 140 restricts pin 142 movement to the proximal-distal direction only. The proximal end 148 of pins 142 may be enlarged to have a width greater than a width of the channels 146 such that the pins 142 are limited in movement along the distal direction. At the distal range of motion limit of pins 142 relative to frame 140, the proximal end 148 of pins 142 engages with a bottom surface 144 of frame 140 to restrict further movement of the pin 142 in the distal direction.

Each of the pins 142 may be coupled with one of the nodes of an array. For example, the proximal end 148 of the pins 142 may be coupled (directly or indirectly) with a top layer of a capacitive pressure sensor. With the frame 140 restricting pin 142 movement to movement along the proximal-distal direction, the frame 140 and pin 142 component may limit capacitance changes due to shear movements and may further decouple nodes of an array. While illustrated as a 6×6 array of pins 142, it should be understood that the frame 140 and pins 142 may be adjusted to corresponding with alternative sensor arrays. Additionally, it should be understood that the frame 140 and pin 142 component is optional.

Figure 21:
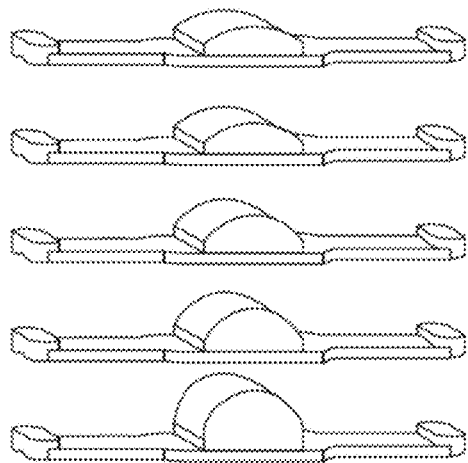
FIG. 21 illustrates curved capacitive sensor arrays according to embodiments of the present disclosure.

In some embodiments, the sensor array may not utilize the frame 140 and pin 142 component and may have a skin-engaging surface. For example, FIG. 21 illustrates a capacitive sensor array 152 where the backing material 154 (e.g., a Kapton film or the like) of the top/distal layer of the capacitive sensor array 152 protrudes from a surrounding surface or base 156 according to some embodiments of the present disclosure. In some embodiments, if the Kapton film includes slits (e.g., slits 88, 90) for decoupling nodes of the array 152, it may be beneficial to provide a flexible coating (e.g., silicone) over the Kapton film for the contact surface of the array 152.

Figure 22:
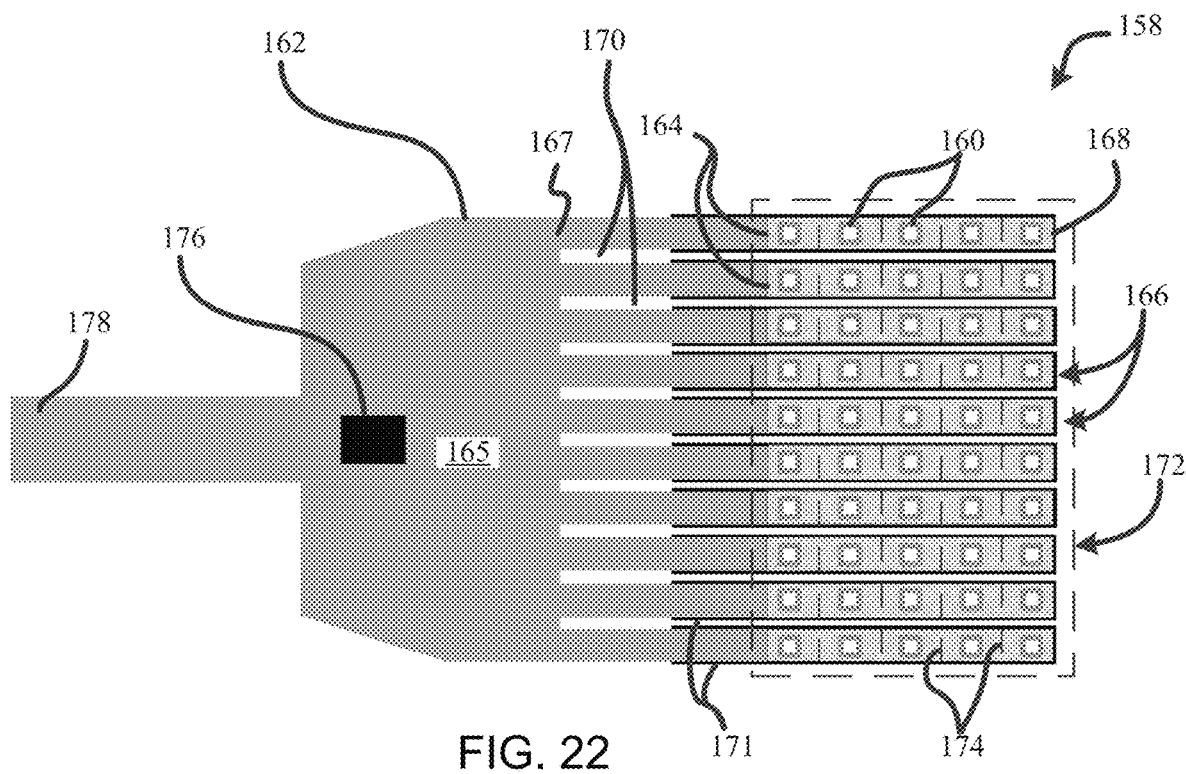
FIG. 22 illustrates a skin engaging surface or distal surface of an exemplary sensor array according to some embodiments of the present disclosure.

While the capacitive sensor arrays described above are generally planar in configuration (with a flat contact surface), some embodiments of the present disclosure may include sensor arrays with a curvature. For example, FIG. 22 illustrates a number of curved capacitive sensor arrays that may be used with device 10 according to embodiments of the present disclosure. The capacitive sensor arrays may be any of the arrays described above. The arrays may have a radius of curvature between 12 mm and 20 mm. The curved array may provide increased coupling between the array and a user's artery when the array is urged against the skin of the user.

Figure 23:
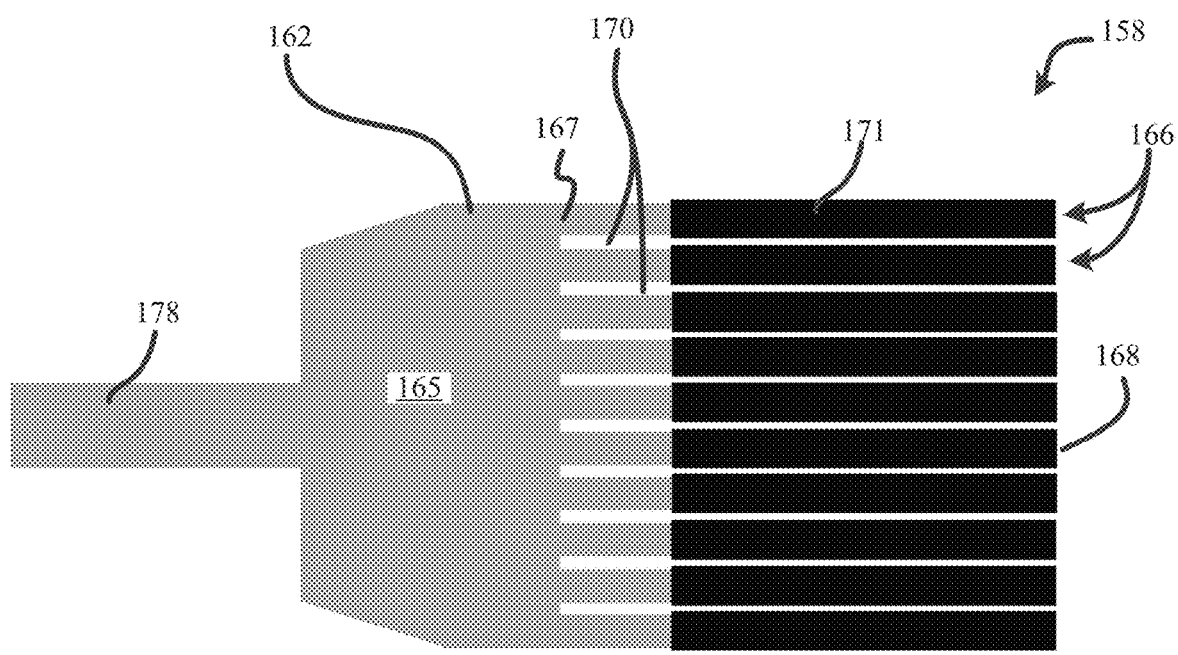
FIG. 23 illustrates a back or proximal surface of the exemplary sensor array of FIG. 22 according to some embodiments of the present disclosure.

FIG. 22 illustrates a skin engaging surface of an exemplary sensor array 158 according to some embodiments of the present disclosure. FIG. 23 illustrates a back or proximal surface of the exemplary sensor array 158 of FIG. 22 according to some embodiments of the present disclosure. The sensor array 158 may include a plurality of capacitive sensing elements 160. The capacitive sensing elements 160 may be formed between a proximal layer 162 and a distal layer 164 (illustrated as a transparent layer for illustration purposes only). The proximal layer 162 may be separated from the distal layer 164 by a dielectric material (not shown), similar to embodiments described above.

The proximal layer 162 may have a "rake" configuration with a plurality of separated cantilevered fingers 166 extending from a platform 165. The fingers 166 may be separated in one axis and each finger 166 may move relative to another. While illustrated with ten fingers 166, it should be understood that more or less fingers 166 may be provided in other embodiments of the disclosure. Each of the fingers 166 may extend from a fixed end 167 to a free end 168 of the fingers 166. Optionally, the fingers 166 may have a width between 1.5-2.0 mm (e.g., 1.75 mm or the like) and a length between 5-30 mm (e.g., 20 mm or the like). Additionally, each of the fingers 166 may form a proximal portion of one or more sensing elements 160, e.g., 1-10 sensing elements, 4-6 sensing elements, or the like. The sensing elements 160 may have a sensing area of 1.0-2.0 mm² (e.g., 1.5 mm² or the like). In some embodiments, the fingers 166 may define rows of the sensing elements 160 of the array 158. The fingers 166 and/or rows of sensing elements 160 of the sensor array 158 may be separated from adjacent fingers 166 and/or rows of sensing elements 160 by slits 170 between the fingers 166 and/or rows of sensing elements 160 of the sensor array 158. The slits 170 may decouple sensing elements 160 on one row from sensing elements 160 on adjacent rows of the sensor array 158 and the slits 170 may have a width of 0.1-0.5 mm (e.g., 0.25 mm or the like).

In some embodiments, the slits 170 and/or fingers 166 may be parallel to one another. Optionally, the sensing area (generally illustrated as dashed box 172) of the sensing array 158 may be toward the free ends 168 of the fingers 166. The length of finger 166 between the fixed end 167 and the sensing area 172 may limit the strain experienced from the fixed end 167 of a finger 166 from propagating to the sensing area 172. Optionally, in some embodiments, a stiffener 171 may be provided on a back surface of each finger 166 to further limit the strain experienced from the fix end 167 of a finger 166 from propagating to the sensing area 172. The stiffener 171 may, in certain embodiments, be a stainless steel material or the like. The stiffener 171 may extend further toward the fixed ends 167 of the fingers 166 than the sensing area 172. Optionally, the stiffener 171 may have a length between 10-15 mm (e.g., 12.5 mm or the like) and may extend through the sensing area 172 to the free end 168 of a finger 166.

The distal layer 164 may be comprised of a series of separate slats, each associated with one of the fingers 166 of the proximal layer 162. The distal layer 164 may form a distal portion of the one or more sensing elements 160. In some embodiments, the distal layer 164 may have one or more slits 174 that extend transverse to a length of the distal layer 164 and that are disposed between adjacent sensing elements 160. The slits 174 may have a length that is less than a width of the distal layer 164. Optionally, the slits 174 may extend from an edge of the distal layer 164 and may optionally extend from an edge that is opposite the edge which an adjacent slit extends from. The slits 174 may increase decoupling between a sensing element 160 and an adjacent sensing element 160 in the same row in the array 158.

In some embodiments, the proximal layer 162 and the distal layer 164 may be a polyimide layer supporting one or more electrodes for forming the sensing elements 160. In some embodiments, the proximal layer 162 may further comprise an integrated circuit 176 on the platform 165. A trace 178 may be parallel to the fingers 166 and may extend from the platform 165 on a side of the platform 165 that is opposite a side in which the fingers 166 extend from. In some embodiments, the electronics may be on the same side as the active area.

Figure 24:
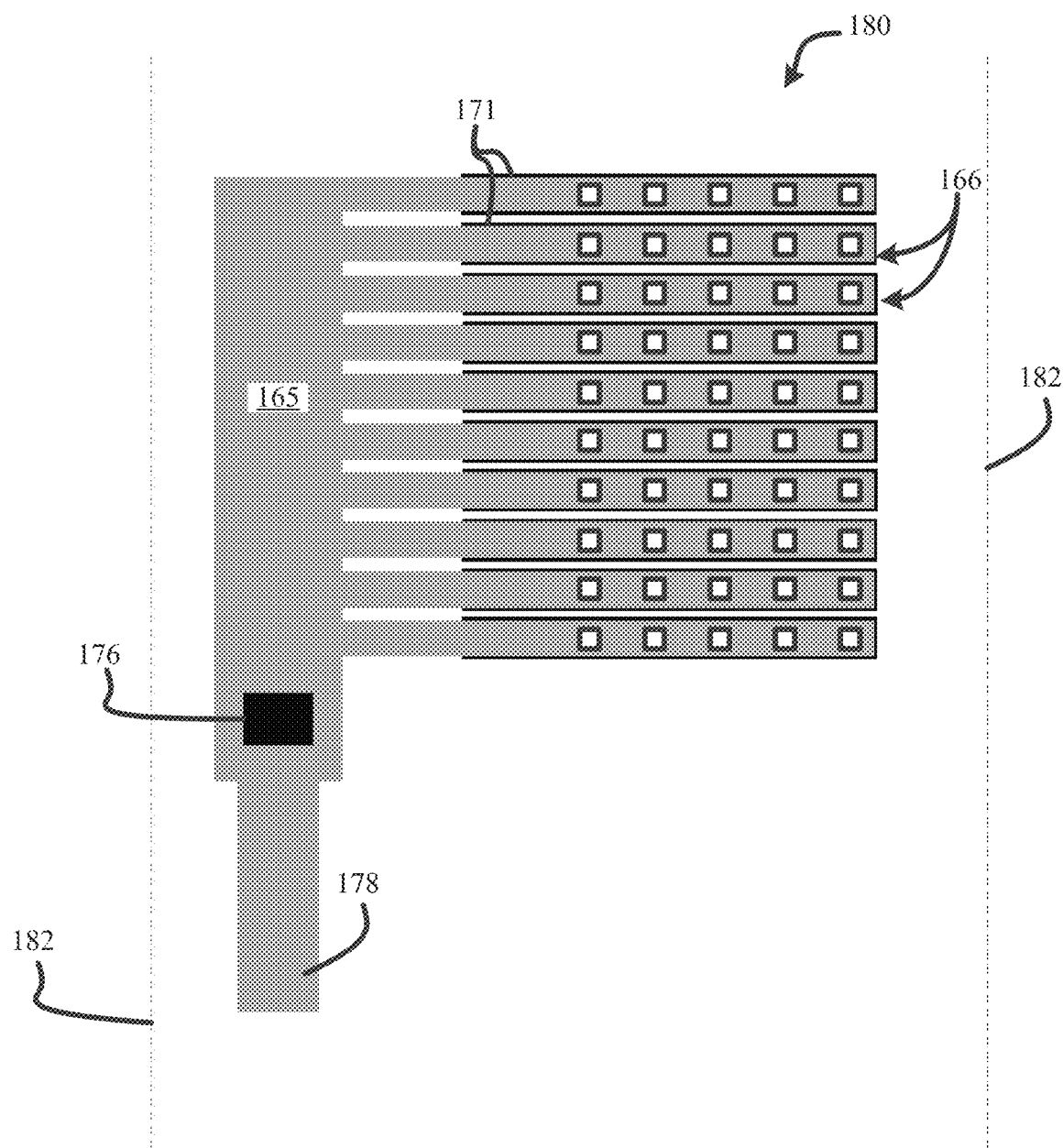
FIG. 24 illustrates an exemplary proximal layer of a sensor array according to some embodiments of the present disclosure.

Optionally, the trace 178 be perpendicular to the fingers 166. For example, FIG. 24 illustrates a proximal layer 180 of a sensor array according to some embodiments of the present disclosure. The proximal layer 180 may include a plurality of separated cantilevered fingers 166 and the fingers 166 may be supported by stiffeners 171, similar to the array 158 described above. However, with proximal layer 180, the trace 178 may extend from the platform 165 in a direction transverse to the length of fingers 166 (e.g., perpendicular to fingers 166 in certain embodiments) to define a "comb" configuration. Such a configuration may be beneficial for use in a wrist-worn device, as the trace 178 and electronics (e.g., IC 176) may extend along a band (shown in phantom 182) of the wrist-worn device.

During use with a wrist-worn device, a length of the fingers 166 may be aligned with a length of the arm when the wrist-worn device is attached to the wrist of the user. This alignment and configuration may allow the array 158 to deform in a cylindrical manner to generally match the wrist geometry. In some embodiments, the free ends 168 of the fingers 166 of the array 158 may be positioned toward the hand of the user when the wrist-worn device is attached to the wrist of the user.

Figure 25:
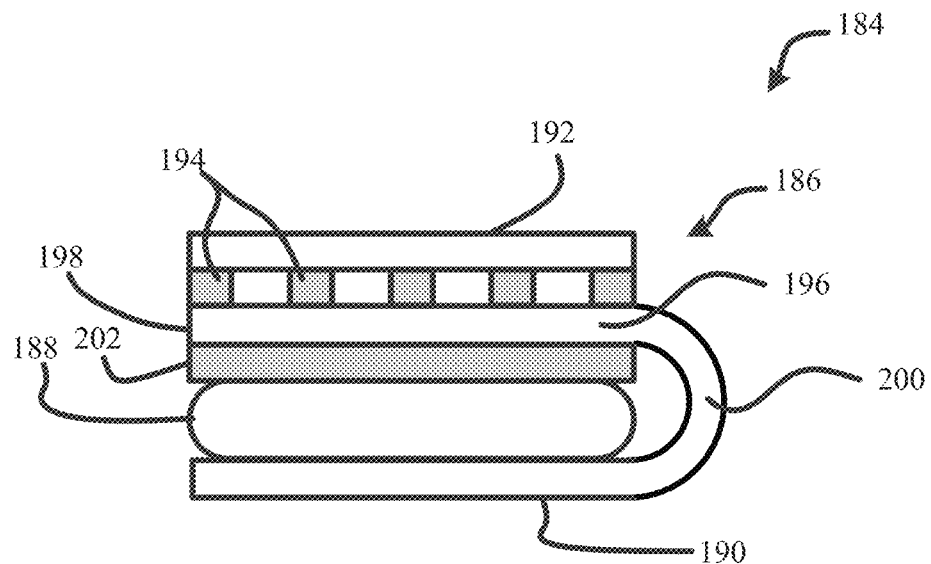
FIG. 25 illustrates an exemplary system according to some embodiments.

Optionally, the fingers of a sensor array may be folded. For example, FIG. 25 illustrates an exemplary system 184 according to some embodiments. The system 184 may comprise a sensor array 186 and an actuator 188. The sensor array 186 may include a proximal layer 190, a distal layer 192, and a dielectric 194 separating the proximal layer 190 and the distal layer 192. The proximal layer 190 and the distal layer 192 may form the capacitive sensing elements of the sensor array 186.

The proximal layer 190 may include one or more fingers 196. The finger 196 may have a free end 198 and may include a bend 200 in the fingers 196. The stiffener 202 may be coupled with a proximal surface of finger 196 that is adjacent the free end 198 of the finger 166. A length of stiffener 202 may be greater than or equal to the length of a distal layer 192 in certain embodiments.

A distal surface of the actuator 188 may be coupled or adhered with the proximal surface of the stiffener 202. In some embodiments, the actuator 188 is sandwiched by the proximal layer 190 such that the proximal layer 190 is on a proximal and distal side of the actuator 188. The actuator 188 may be a fluid or air bladder or the like and may be configured for driving the sensing portion of the array 186 into the tissue of the user (e.g., for an applanation sweep, measuring blood pressure morphology, or the like).

Figure 26:
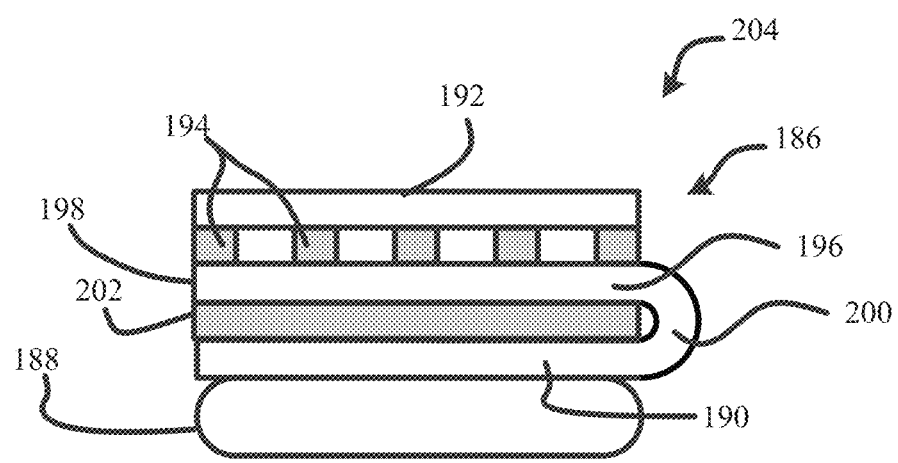
FIG. 26 illustrates another exemplary system according to some embodiments of the present disclosure.

Optionally, in some embodiments, the actuator 188 may be coupled to a proximal side of sensor array 186. For example, FIG. 26 illustrates another exemplary system 204 according to some embodiments of the present disclosure. System 204 includes a sensor array 186 coupled with an actuator 188, similar to system 184 of FIG. 25, however actuator 188 is coupled with a proximal side of the sensor array 186 rather than being sandwiched between the proximal layer 190.

Figure 27:
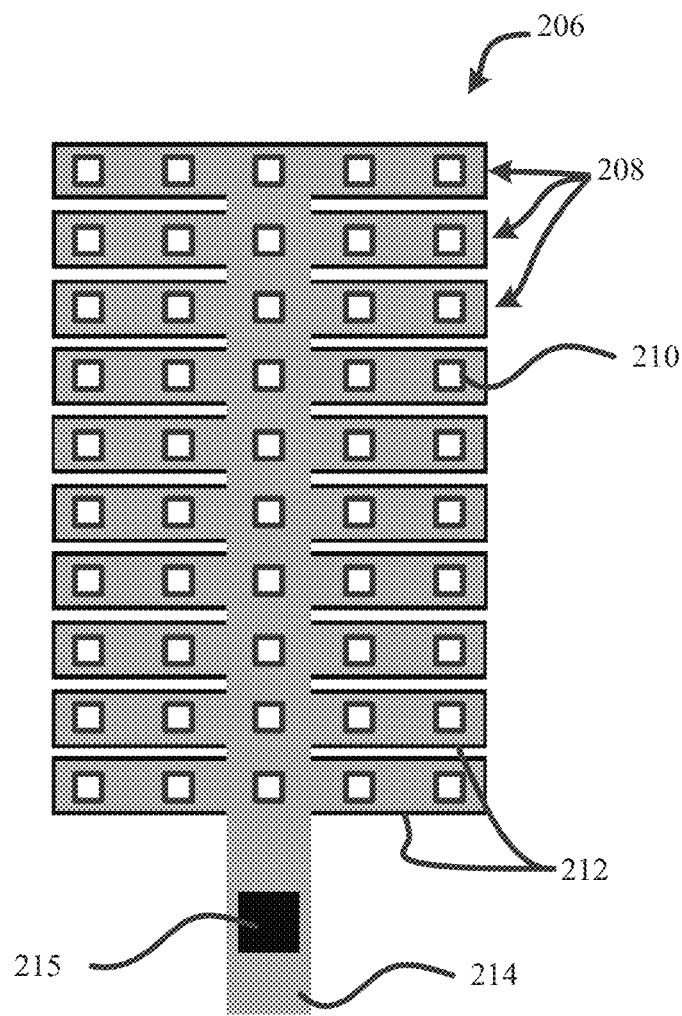
FIG. 27 illustrates another exemplary proximal layer of another exemplary sensor array according to some embodiments of the present disclosure.

FIG. 27 illustrates another exemplary proximal layer 206 of another exemplary sensor array according to some embodiments of the present disclosure. The proximal layer 206 may comprise a plurality of fingers 208 which form one or more sensing areas 210 of the sensor array. Additionally, the plurality of fingers 208 may each be supported by a stiffener 212. However, in contrast with the configurations described above, the plurality of fingers 208 may be coupled with one another along a central portion of each finger 208 and the trace 214 may extend from the central portion of the finger 208 at the edge of the proximal layer 206. The integrated circuit 215 may be coupled with the trace 214 in certain embodiments.

Figure 28:
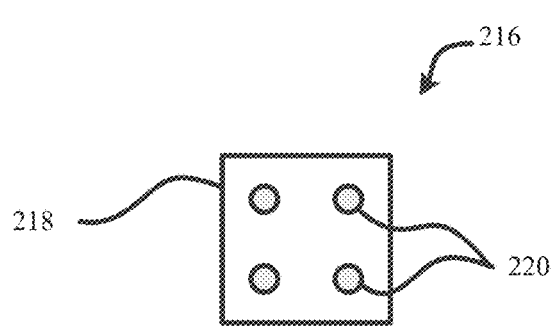
FIG. 28 illustrates an exemplary pillar configuration for a sensing element that may be used to support a proximal electrode relative to a distal electrode in any of the herein described embodiments.

FIG. 28 illustrates an exemplary pillar configuration 216 for a sensing element 218 that may be used to separate a proximal layer from a distal layer in any of the above described embodiments. Pillar configuration 216 comprises a two by two array of dielectric pillars 220 for supporting a proximal electrode relative to a distal electrode of a capacitive pressure sensing element. The two by two array of dielectric pillars 220 may be disposed in the sensing area of sensing element 218. While illustrated as a two by two array of dielectric pillars 220, larger arrays may be used in other embodiments (e.g., three by three or the like).

Figure 29:
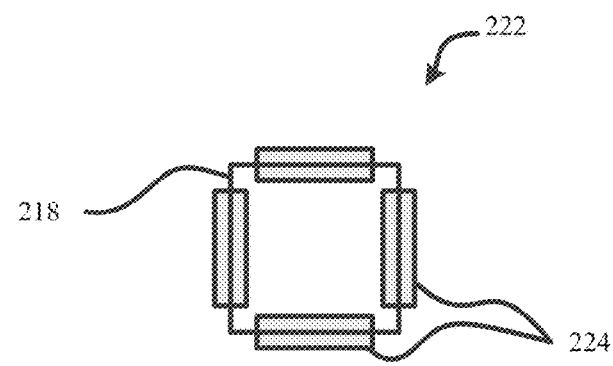
FIG. 29 illustrates another exemplary pillar configuration for a sensing element that may be used to support a proximal electrode relative to a distal electrode in any of the herein described embodiments.

FIG. 29 illustrates another exemplary pillar configuration 222 for a sensing element 218 that may be used to support a proximal electrode relative to a distal electrode in any of the above described embodiments. Pillar configuration 222 comprises four dielectric strips 224. The dielectric strips 224 may have a length less than the width of the sensing element 218. The dielectric strips 224 may be centered and disposed on each edge of the sensing element 218 to support a proximal electrode relative to a distal electrode of a capacitive pressure sensing element. In some embodiments, the dielectric strips 224 may straddle the edge of the sensing element 218. While illustrated as including four strips 224, it should be understood that fewer or more strips may be used in other embodiments. For example, in some embodiments, the strips 224 may be disposed only one two of the edges of the sensing element 218. Optionally, multiple smaller strips may be disposed on a single edge of the sensing element 218.

Figure 30:
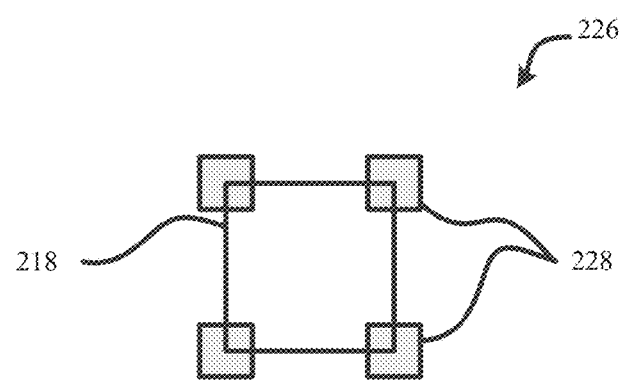
FIG. 30 illustrates yet another exemplary pillar configuration for a sensing element that may be used to support a proximal electrode relative to a distal electrode in any of the herein described embodiments.

FIG. 30 illustrates yet another exemplary pillar configuration 226 for a sensing element 218 that may be used to support a proximal electrode relative to a distal electrode in any of the above described embodiments. Pillar configuration 226 may comprise a two by two array of dielectric pillars 228. The dielectric pillars 228 may be disposed at the corners of the sensing element 218. In some embodiments, the pillars 228 are only partially disposed within the sensing area of the sensing element 218. The pillar pattern may also be a mix of side support (FIG. 29), corner support (FIG. 30) and center support (FIG. 28).

While the above sensor configurations are described generally for use with capacitive pressure sensors, it should be understood that the configurations described herein may be applicable to other pressure sensors (e.g., piezoresistive pressure sensors or the like).

Additionally, in some embodiments, blood pressure morphology and/or absolute pressure measurements. In certain embodiments, peripheral blood pressure waveform (e.g., from radial artery or the like) may be measured with embodiments described above (e.g., with a wrist-worn device or the like). A transfer function may be applied to the blood pressure waveform to calculate a central aortic waveform. From the calculated central aortic waveform, an augmentation index may be calculated which may be equal to the augmentation pressure over the actual left ventricle ejected pressure. The augmentation index may be an indicator for arterial health (e.g., stiffness and/or aging). This arterial health may then be correlated to other physiologies, stress, drug effects, pathophysiologies, etc.

It will be appreciated that personal information data may be utilized in a number of ways to provide benefits to a user of a device. For example, personal information such as health or biometric data may be utilized for convenient authentication and/or access to the device without the need of a user having to enter a password. Still further, collection of user health or biometric data (e.g., blood pressure measurements) may be used to provide feedback about the user's health and/or fitness levels. It will further be appreciated that entities responsible for collecting, analyzing, storing, transferring, disclosing, and/or otherwise utilizing personal information data are in compliance with established privacy and security policies and/or practices that meet or exceed industry and/or government standards, such as data encryption. For example, personal information data should be collected only after receiving user informed consent and for legitimate and reasonable uses of the entity and not shared or sold outside those legitimate and reasonable uses. Still further, such entities would take the necessary measures for safeguarding and securing access to collected personal information data and for ensuring that those with access to personal information data adhere to established privacy and security policies and/or practices. In addition, such entities may be audited by a third party to certify adherence to established privacy and security policies and/or practices. It is also contemplated that a user may selectively prevent or block the use of or access to personal information data. Hardware and/or software elements or features may be configured to block use or access. For instance, a user may select to remove, disable, or restrict access to certain health related applications that collect personal information, such as health or fitness data. Alternatively, a user may optionally bypass biometric authentication methods by providing other secure information such as passwords, personal identification numbers, touch gestures, or other authentication methods known to those skilled in the art.

One or more computing devices may be adapted to provide desired functionality by accessing software instructions rendered in a computer-readable form. When software is used, any suitable programming, scripting, or other type of language or combinations of languages may be used to implement the teachings contained herein. However, software need not be used exclusively, or at all. For example, some embodiments of the methods and systems set forth herein may also be implemented by hard-wired logic or other circuitry, including but not limited to application-specific circuits. Combinations of computer-executed software and hard-wired logic or other circuitry may be suitable as well.

Embodiments of the methods disclosed herein may be executed by one or more suitable computing devices. Such system(s) may comprise one or more computing devices adapted to perform one or more embodiments of the methods disclosed herein. As noted above, such devices may access one or more computer-readable media that embody computer-readable instructions which, when executed by at least one computer, cause the at least one computer to implement one or more embodiments of the methods of the present subject matter. Additionally or alternatively, the computing device(s) may comprise circuitry that renders the device(s) operative to implement one or more of the methods of the present subject matter.

Any suitable computer-readable medium or media may be used to implement or practice the presently-disclosed subject matter, including but not limited to, diskettes, drives, and other magnetic-based storage media, optical storage media, including disks (e.g., CD-ROMS, DVD-ROMS, variants thereof, etc.), flash, RAM, ROM, and other memory devices, and the like.

The subject matter of embodiments of the present disclosure is described here with specificity, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

Different arrangements of the components depicted in the drawings or described above, as well as components and steps not shown or described are possible. Similarly, some features and sub-combinations are useful and may be employed without reference to other features and sub-combinations. Embodiments of the disclosure have been described for illustrative and not restrictive purposes, and alternative embodiments will become apparent to readers of this patent. Additionally, it should be understood that the ranges and materials provided herein are exemplary and that the ultimate selection of sizes, materials, etc. may depend on the overall device design and application. Accordingly, the present disclosure is not limited to the embodiments described above or depicted in the drawings, and various embodiments and modifications may be made without departing from the scope of the claims below.

What is claimed is:

1. A wrist-worn device configured to measure blood pressure of a user wearing the wrist-worn device, the wrist-worn device comprising:
a sensor array comprising capacitive nodes configured to measure blood pressure of a user wearing the wrist-worn device, the sensor array comprising one or more distal electrodes and one or more proximal electrodes, wherein each of the capacitive nodes is formed via one of the one or more distal electrodes and one of the one or more proximal electrodes that are separated by a respective gap, wherein each of the one or more distal electrodes is configured to be disposed between a skin of the user and a respective one of the one or more proximal electrodes, and wherein the capacitive nodes are formed at laterally spaced apart locations;
a dielectric layer disposed between the one or more distal electrodes and the one or more proximal electrodes;
wherein a distal surface of each of the capacitive nodes protrudes toward the skin of the user to form a protrusion individual to the capacitive node;
wherein the dielectric layer includes laterally spaced apart pillars, each of the laterally spaced apart pillars being positioned at a respective one of the capacitive nodes and supporting a corresponding one of the one or more distal electrodes relative to a corresponding one of the one or more proximal electrodes of the respective one of the capacitive nodes.

2. The wrist-worn device of claim 1, wherein:
one of the one or more distal electrodes is formed by a sheet of conductive material;
the one or more proximal electrodes comprise two or more proximal electrodes; and
each of two or more of the capacitive nodes comprises a respective one of the two or more proximal electrodes in combination with the distal electrode formed by the sheet of conductive material.

3. The wrist-worn device of claim 2, wherein the sheet of conductive material comprises a conductive silicone.

4. The wrist-worn device of claim 1, wherein the one or more proximal electrodes comprise independent proximal electrodes.

5. The wrist-worn device of claim 1, wherein the one or more proximal electrodes comprise proximal electrodes that form strips of the proximal electrodes running parallel with one another.

6. The wrist-worn device of claim 1, wherein each of the laterally spaced apart pillars of the dielectric layer has a circular cross-section.

7. The wrist-worn device of claim 1, wherein each of the laterally spaced apart pillars of the dielectric layer has a rectangular cross-section.

8. The wrist-worn device of claim 1, wherein the dielectric layer includes strips supporting the one or more distal electrodes relative to the one or more proximal electrodes, the strips of the dielectric layer being positioned in spaces between adjacent capacitive nodes of the capacitive nodes.

9. The wrist-worn device of claim 1, comprising a device band having a length and a width, wherein:
the sensor array is supported by the device band;
the sensor array comprises primary slits, each of the primary slits being disposed between adjacent capacitive nodes of the capacitive nodes and extending along the width of the device band; and
the sensor array comprises secondary lateral slits, each of the secondary lateral slits extending from a corresponding one of the primary slits in a direction transverse to the primary slit, each of the secondary lateral slits at least partially separating adjacent capacitive nodes of the capacitive nodes.

10. The wrist-worn device of claim 1, wherein:
the capacitive nodes are arranged in rows and columns; and
adjacent rows of the capacitive nodes are staggered.

11. The wrist-worn device of claim 1, wherein the sensor array is curved.

12. The wrist-worn device of claim 11, wherein the sensor array has a radius of curvature between 12 mm and 20 mm.

13. The wrist-worn device of claim 1, further comprising pins and a frame, each of the pins coupled with one of the capacitive nodes of the sensor array, wherein the pins are restricted to movement in the a proximal-distal direction by the frame.

14. A wrist-worn device configured to measure blood pressure of a user wearing the wrist-worn device, the wrist-worn device comprising:
a sensor array comprising capacitive nodes, the sensor array comprising a sheet of conductive material and proximal electrodes that are spaced apart, wherein the sheet of conductive material is separated from each of the proximal electrodes by a respective gap, wherein each of the capacitive nodes is formed at spaced apart locations where the sheet of conductive material overlaps with a respective one of the proximal electrodes,
wherein the sensor array comprises primary slits, each of the primary slits being disposed between adjacent capacitive nodes of the capacitive nodes and extending along a width of the device band, and
wherein the sensor array comprises secondary lateral slits, each of the secondary lateral slits extending from a corresponding one of the primary slits in a direction transverse to the primary slit, each of the secondary lateral slits at least partially separating adjacent capacitive nodes of the capacitive nodes.

15. The wrist-worn device of claim 14, wherein:
the capacitive nodes are arranged in rows and columns; and
adjacent rows of the capacitive nodes are staggered.

16. The wrist-worn device of claim 14, wherein each of the proximal electrodes is configured as an individual electrode.

17. The wrist-worn device of claim 14, wherein the sensor array is curved.

18. The wrist-worn device of claim 17, wherein the sensor array has a radius of curvature between 12 mm and 20 mm.

19. The wrist-worn device of claim 14, further comprising pins and a frame, each of the pins being coupled with one of the capacitive nodes, wherein the pins are restricted to movement in a proximal-distal direction by the frame.

20. The wrist-worn device of claim 14, comprising a device band having a length and a width, wherein the sensor array is supported by the device band.

21. The wrist-worn device of claim 14, further comprising a dielectric layer disposed between the sheet of conductive material and the proximal electrodes.

22. The wrist-worn device of claim 21, wherein the dielectric layer includes pillars that are spaced apart, each of the pillars being disposed at a respective one of the capacitive nodes and supporting the sheet of conductive material relative to one of the proximal electrodes corresponding to the respective one of the capacitive nodes.

23. The wrist-worn device of claim 22, wherein each of the pillars has a circular cross-section.

24. The wrist-worn device of claim 22, wherein each of the pillars has a rectangular cross-section.

25. The wrist-worn device of claim 21, wherein the dielectric layer includes strips supporting the sheet of conductive material relative to the proximal electrodes, the strips of the dielectric layer being positioned in spaces between adjacent capacitive nodes of the capacity nodes.

26. A wrist-worn device configured to measure blood pressure of a user wearing the wrist-worn device, the wrist-worn device comprising:
a device band having a length and a width;
a sensor array supported by the device band and comprising capacitive nodes configured to measure blood pressure of a user wearing the wrist-worn device, the sensor array comprising one or more distal electrodes and one or more proximal electrodes, wherein the distal and proximal electrodes are each of the capacitive nodes is formed via one of the one or more distal electrodes and one of the one or more proximal electrodes that are separated by a respective gap, wherein each of the one or more distal electrodes is configured to be disposed between a skin of the user and a respective one of the one or more proximal electrodes, and wherein the capacitive nodes are formed at laterally spaced apart locations;
wherein the sensor array comprises primary slits, each of the primary slits being disposed between adjacent capacitive nodes of the capacitive nodes and extending along the width of the device band, and
wherein the sensor array comprises secondary slits, each of the secondary slits extending from a corresponding one of the primary slits in a direction transverse to the primary slit, each of the secondary slits at least partially separating adjacent capacitive nodes of the capacitive nodes.

27. The wrist-worn device of claim 26, wherein:
the capacitive nodes are arranged in rows and columns; and
adjacent rows of the capacitive nodes are staggered.

28. The wrist-worn device of claim 26, wherein at least one of:
the one or more distal electrodes form strips of the one or more distal electrodes that extend parallel to one another; and
the one or more proximal electrodes form strips of the one or more proximal electrodes that extend parallel to one another.

29. The wrist-worn device of claim 26, wherein the sensor array is curved.

30. The wrist-worn device of claim 29, wherein the sensor array has a radius of curvature between 12 mm and 20 mm.

31. The wrist-worn device of claim 26, further comprising pins and a frame, each of the pins being coupled with one of the capacitive nodes, wherein the pins are restricted to movement in the a proximal-distal direction by the frame.

32. A wrist-worn device configured to measure blood pressure of a user wearing the wrist-worn device, the wrist-worn device comprising:
a sensor array comprising capacitive nodes configured to measure blood pressure of a user wearing the wrist-worn device, the sensor array comprising:
one or more distal electrodes and one or more proximal electrodes, wherein each of the capacitive nodes is formed via one of the one or more distal electrodes and one of the one or more proximal electrodes that are separated by a respective gap, and wherein the capacitive nodes are formed at laterally spaced apart locations;
a dielectric layer disposed between the one or more distal electrodes and the one or more proximal electrodes, the dielectric layer including pillars that are spaced apart, each of the pillars being positioned at a respective one of the capacitive nodes and supporting the distal electrode a corresponding one of the one or more distal electrodes relative to a corresponding one of the one or more proximal electrodes of the respective one of the capacitive nodes,
wherein a distal surface of each of the capacitive nodes protrudes toward a skin of the user to form a protrusion individual to the capacitive node.

33. The wrist-worn device of claim 32, wherein each of the pillars has a circular cross-section.

34. The wrist-worn device of claim 32, wherein each of the pillars has a rectangular cross-section.

35. A wrist-worn device configured to measure blood pressure of a user wearing the wrist-worn device, the wrist-worn device comprising:
a sensor array comprising a proximal layer, a distal layer, and a dielectric layer disposed between the proximal layer and the distal layer, the dielectric layer supporting the proximal layer relative to the distal layer, the proximal layer comprising proximal electrodes, the distal layer comprising distal electrodes, and wherein capacitive nodes of the sensor array are formed at locations where a distal electrode of the distal electrodes overlaps with a proximal electrode of the proximal electrodes;
wherein the proximal layer comprises cantilevered fingers, each of the cantilevered fingers being separated from an adjacent one of the cantilevered fingers by an intervening slit, and wherein the cantilevered fingers are folded.

36. The wrist-worn device of claim 35, wherein each of the cantilevered fingers are parallel with one another.

37. The wrist-worn device of claim 35, further comprising stiffeners, each of the stiffeners being coupled with one of the cantilevered fingers.

38. The wrist-worn device of claim 35, further comprising an actuator sandwiched by the cantilevered fingers.

39. The wrist-worn device of claim 38, further comprising stiffeners, each of the stiffeners being coupled with one of the cantilevered fingers adjacent to a free end of the cantilevered finger; and wherein the actuator is coupled with each of the stiffeners.

* * * * *